(12) United States Patent
Morimoto et al.

(10) Patent No.: US 11,730,450 B2
(45) Date of Patent: Aug. 22, 2023

(54) ULTRASONIC OSCILLATOR UNIT AND ULTRASONIC ENDOSCOPE USING SAME

(71) Applicant: FUJIFILM Corporation, Tokyo (JP)

(72) Inventors: Yasuhiko Morimoto, Ashigarakami-gun (JP); Katsuya Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 780 days.

(21) Appl. No.: 16/139,643

(22) Filed: Sep. 24, 2018

(65) Prior Publication Data

US 2019/0021696 A1    Jan. 24, 2019

Related U.S. Application Data

(63) Continuation of application No. PCT/JP2017/006963, filed on Feb. 24, 2017.

(30) Foreign Application Priority Data

Apr. 1, 2016 (JP) ................. 2016-074448

(51) Int. Cl.
*A61B 8/00* (2006.01)
*A61B 8/12* (2006.01)
(Continued)

(52) U.S. Cl.
CPC .............. *A61B 8/4455* (2013.01); *A61B 8/12* (2013.01); *A61B 8/445* (2013.01); *A61B 8/4483* (2013.01);
(Continued)

(58) Field of Classification Search
CPC ... A61B 8/4455; A61B 8/4483; A61B 8/4494; A61B 8/445; A61B 8/12; A61B 1/00114; A61B 8/4461; H04R 17/00; B06B 1/0625
See application file for complete search history.

(56) References Cited

U.S. PATENT DOCUMENTS 6,063,035 A      5/2000  Sakamoto et al.
2002/0156373 A1* 10/2002 Wakabayashi ........ B06B 1/0622
                                                    600/437

(Continued)

FOREIGN PATENT DOCUMENTS

CN    1726872 A    2/2006
CN    101396289 A  4/2009
(Continued)

OTHER PUBLICATIONS

English Translation of KR-20040076219-A (Year: 2004).*

(Continued)

*Primary Examiner* — Ashley K Buran
*Assistant Examiner* — Helene Bor
(74) *Attorney, Agent, or Firm* — Birch, Stewart, Kolasch & Birch, LLP

(57) ABSTRACT

The ultrasonic oscillator unit has: an ultrasonic oscillator array in which a plurality of ultrasonic oscillators are arranged; an electrode part having a plurality of electrodes provided on an end surface side of the ultrasonic oscillator array and electrically connected to the plurality of ultrasonic oscillators, respectively; a backing material layer that is disposed on a back surface of the ultrasonic oscillator array, has an outer surface having a circular-arc cross-section and is provided with a recess on the inside thereof opposite to the outer surface; a wiring board having a plurality of wiring lines electrically connected to the plurality of electrodes of the electrode part; and a cable wiring part in which a plurality of cables connected to the plurality of wiring lines, respectively, are wiring-connected; at least a portion of the cable wiring part being included in the recess of the backing material layer.

19 Claims, 9 Drawing Sheets

(51) Int. Cl.
   *H04R 17/00* (2006.01)
   *B06B 1/06* (2006.01)
   *A61B 1/00* (2006.01)
   *A61B 1/018* (2006.01)
(52) U.S. Cl.
   CPC .......... *A61B 8/4494* (2013.01); *B06B 1/0625* (2013.01); *H04R 17/00* (2013.01); *A61B 1/00082* (2013.01); *A61B 1/00096* (2013.01); *A61B 1/00114* (2013.01); *A61B 1/018* (2013.01); *A61B 8/4416* (2013.01); *A61B 8/4461* (2013.01)

(56) References Cited

U.S. PATENT DOCUMENTS

| | | | |
|---|---|---|---|
| 2006/0058706 A1* | 3/2006 | Frey | G10K 11/004 601/2 |
| 2008/0249404 A1 | 10/2008 | Mikkaichi et al. | |
| 2009/0088646 A1 | 4/2009 | Nagano et al. | |
| 2009/0093725 A1 | 4/2009 | Sato et al. | |
| 2010/0204583 A1 | 8/2010 | Rhim et al. | |
| 2010/0241004 A1* | 9/2010 | Jung | A61B 8/4444 600/459 |
| 2011/0316389 A1 | 12/2011 | Kwon et al. | |
| 2014/0058269 A1 | 2/2014 | Irie | |
| 2014/0121526 A1 | 5/2014 | Matsumoto et al. | |
| 2016/0183914 A1 | 6/2016 | Fujimura | |
| 2016/0296975 A1* | 10/2016 | Lukacs | B06B 1/0685 |

FOREIGN PATENT DOCUMENTS

| | | | | |
|---|---|---|---|---|
| CN | 203074661 U | 7/2013 | | |
| CN | 103583055 A | 2/2014 | | |
| EP | 1621135 A1 | 2/2006 | | |
| JP | 3-173544 A | 7/1991 | | |
| JP | H06225395 A | * | 8/1994 | |
| JP | 8-4359 A | 1/1996 | | |
| JP | 2004-363746 A | 12/2004 | | |
| JP | 3802756 B2 | 7/2006 | | |
| JP | 4445764 B2 | 4/2010 | | |
| JP | 2010-184114 A | 8/2010 | | |
| JP | 4980653 B2 | 7/2012 | | |
| JP | 5399594 B1 | 1/2014 | | |
| KR | 20040076219 A | * | 8/2004 | ............... B63J 2/10 |
| WO | WO 2015/053044 A1 | 4/2015 | | |
| WO | WO-2016017842 A1 | * | 2/2016 | ............... A61B 8/12 |

OTHER PUBLICATIONS

English Translation of JP-H06225395-A (Year: 1944).*
English Translation of WO-2016017842-A1 (Year: 2016).*
Chinese Office Action and Search Report dated Aug. 27, 2020 for Application No. 201780020045.7 with an English translation of the Office Action.
European Office Action for European Application No. 17773919.0, dated Apr. 22, 2020.
International Preliminary Report on Patentability (Form PCT/IPEA/409) for International Application No. PCT/JP2017/006963, dated Oct. 23, 2017, with English translation.
International Search Report and Written Opinion of the International Searching Authority (Forms PCT/ISA/210 and PCT/ISA/237) for International Application No. PCT/JP2017/006963, dated May 23, 2017, with English translation of the International Search Report.
Extended European Search Report for European Application No. 17773919.0, dated Mar. 15, 2019.

* cited by examiner

ULTRASONIC OSCILLATOR UNIT AND ULTRASONIC ENDOSCOPE USING SAME

CROSS-REFERENCE TO RELATED APPLICATIONS

This application is a Continuation of PCT International Application No. PCT/JP2017/006963 filed on Feb. 24, 2017, which claims priority under 35 U.S.C § 119(a) to Japanese Patent Application No. 2016-074448 filed on Apr. 1, 2016. Each of the above application(s) is hereby expressly incorporated by reference, in its entirety, into the present application.

BACKGROUND OF THE INVENTION

1. Field of the Invention

The present invention relates to an ultrasonic oscillator unit and an ultrasonic endoscope using the same, and particularly, to an ultrasonic oscillator unit having an ultrasonic oscillator wiring structure for realizing micro ultrasonic oscillators used for an ultrasonic endoscope to be inserted into a body cavity, and an ultrasonic endoscope using the same.

2. Description of the Related Art

Ultrasonic endoscopes are ones in which an ultrasonic observation part is provided at a distal end part of an endoscope with observation of the gallbladder or the pancreas by an alimentary canal as a main purpose. In order to safely insert the ultrasonic endoscope into the alimentary canal, an optical sensor, illumination means, an air supply port, a water supply port, and a suction port in addition to the ultrasonic observation part are provided at the distal end part of the ultrasonic endoscope, similarly to ordinary endoscopes that are not provided with the ultrasonic observation part. For that reason, the external diameter of the distal end part of the ultrasonic endoscope increases, and causes a decrease in the operability of the ultrasonic endoscope and an increase in the burden on a patient into which the distal end part of the ultrasonic endoscope is to be inserted.

Thus, in order to improve the operability of the ultrasonic endoscope and mitigate the burden on the patient, the ultrasonic observation part is required to be small-sized. Thus, in recent years, various proposals, such as improving the workability in wiring work and making the ultrasonic observation part of the ultrasonic endoscope small-sized are made (refer to JP4445764B, JP5399594B, JP1996-004359B (JP-H08-004359B), JP4980653B, and JP3802756B).

JP4445764B discloses an ultrasonic oscillator unit having an ultrasonic oscillator array that has an acoustic matching layer, piezoelectric elements, and a back surface damping layer; a rigid board electrically connected to the respective piezoelectric elements in the vicinity of a central part of the ultrasonic oscillator array in a width direction thereof; a signal cable bundle including a plurality of signal core wires; and a flexible printed wiring board that is interposed between the rigid board and the signal cable bundle to electrically connect both. Moreover, the ultrasonic oscillator array, and the cable bundle and the flexible printed wiring board are separate structures, both are connected to each other using thermocompression bonding as a means, and thereafter, the flexible printed wiring board is configured in a multiple-folded form.

JP5399594B discloses an ultrasonic endoscope having an ultrasonic transmission/reception unit that transmits and receives ultrasonic waves; a wiring board electrically connected to a back side of the ultrasonic transmission/reception unit; a plurality of driver wires electrically connected to the wiring board; and a housing that houses the wiring board to hold the ultrasonic transmission/reception unit. The wiring board has a rigid circuit board electrically connected to a plurality of ultrasonic oscillators in the vicinity of central parts thereof in a width direction; and an enveloping part that wraps and bundles the driver wires, and is inserted into a housing in a state where the driver wires are wrapped and bundled by the enveloping part.

JP-H08-004359B discloses an ultrasound probe in which signal lines are alternately connected from both sides of an ultrasonic oscillator array disposed on a convex surface and electrodes are led out from one side surface side by a single flexible printed wiring board having conductive paths formed on both surfaces thereof.

JP4980653B discloses an electronic scanning type ultrasound probe having respective pad electrodes of a pad electrode group that are arranged on an oscillator board of an ultrasonic oscillator unit so as to extend from the vicinity of a central part of the ultrasonic oscillator array in a width direction thereof and that are electrically connected to ultrasonic oscillators; and a coaxial cable assembly having a comb-like lead electrode group. Upon connection between the pad electrodes of the ultrasonic oscillator unit and leads of the coaxial cable assembly, alignment between the respective pad electrodes and the comb-like lead electrode group is performed.

JP3802756B discloses an ultrasound probe including a printed board having first and second signal pattern groups electrically connected to electrodes of an ultrasonic oscillator array in the vicinity of a central part of the ultrasonic oscillator array in a width direction thereof and electrically connected to halves of the electrodes of the ultrasonic oscillator array, respectively. The first and second signal pattern groups are wired with the coaxial cable in different directions, respectively.

SUMMARY OF THE INVENTION

Meanwhile, in the ultrasonic endoscopes disclosed in JP4445764B, JP5399594B, JP-H08-004359B, JP4980653B, and JP3802756B, numerous ultrasonic oscillators are disposed in an array on the ultrasonic observation part provided at a distal end part, and cables are respectively wired to the ultrasonic oscillator. For example, the number of channels is as large as, for example, 48 to 192, the external diameter of ultrasonic observation part is small, and expensive, extremely fine cables are used as the cables. Therefore, in the current situation, wiring within the ultrasonic observation part is a complicated task, and numerous wiring lines are manually wired within a small distal end part. For this reason, the handling of the cables within the ultrasonic observation part with a small external diameter is complicated, and high filling is required. That is, since it is necessary to wire the cables in high density within the ultrasonic observation part in addition to the handling of the cables being complicated, this becomes a causer that the workability is poor and the manufacturing costs of the ultrasonic endoscope become high.

In spite of size reduction of the ultrasonic observation part being required in order to improve the operability and reduce the burden on the patient, as described above, there is a problem that the size reduction of the ultrasonic observation part is very difficult from viewpoints of the manufacture stability of the ultrasonic observation part, and the manufacturing costs thereof.

Additionally, in the techniques disclosed in JP4445764B and JP1996-004359B, a structure in which the flexible printed wiring board of the ultrasonic oscillator unit is folded up is provided. Therefore, there is a problem that the wiring structure of the cable bundle and the flexible printed wiring board is complicated. Additionally, although the ultrasonic oscillator array, and the cable bundle and the flexible printed wiring board are connected to each other by thermocompression bonding, there is still a problem in the workability of the wiring. Particularly, in JP4445764B, there are problems that, during the manufacture of the ultrasonic oscillator unit, a burden, for example, a load is applied on a cable in a case where the flexible printed wiring board is folded up multiple times, and the cable wiring line to which the load is applied is disconnected.

Additionally, in the techniques disclosed in JP5399594B, JP4980653B, and JP3802756B, the workability of the wiring work is reduced by using a simple configuration. However, inspection of the quality of the ultrasonic oscillators used for the ultrasonic endoscope is allowed for the first time after the wiring between the ultrasonic oscillators and the cables is completed. For this reason, since there is a constant yield rate, in a case where there a problem in the quality of the ultrasonic oscillators, all components and materials that are used for the ultrasonic oscillator and the wiring lines of the ultrasonic oscillators, such as a large number of wired fine and expensive cables, cannot be used and become useless. Therefore, there is a problem that loss is large and the manufacturing costs of the ultrasonic endoscope become high.

Additionally, in any of the techniques disclosed in JP4445764B, JP5399594B, JP4980653B, and JP3802756B, the electrodes of the ultrasonic oscillator array and the wiring board are electrically connected to each other in the vicinity of the central part of the ultrasonic oscillator array in the width direction thereof. In this structure, there are problems that the manufacture is significantly difficult and the success rate of the manufacture is not high.

An object of the invention is to solve the above problems of the related arts and to provide an ultrasonic oscillator unit that can be small-sized, has excellent workability in a case where respective electrodes of an ultrasonic oscillator array and numerous cables are wired, has low difficulty of an operation step, has a wiring structure in which a load on a cable is unlikely to occur and there is less risk of disconnection, and is suitable for use in an ultrasonic endoscope, and an ultrasonic endoscope using the same.

Additionally, another object of the invention is to solve the above problems of the related arts and to provide an ultrasonic oscillator unit that is capable of inspecting an ultrasonic oscillator array before cable wiring, has high manufacture stability, and does not cause an increase in cost, and is suitable for use in an ultrasonic endoscope, and an ultrasonic endoscope using the same, in addition to the above object.

In order to achieve the above object, an ultrasonic oscillator unit of the invention comprises an ultrasonic oscillator array in which a plurality of ultrasonic oscillators are arranged outward in a circular-arc shape; an electrode part having a plurality of electrodes provided on an end surface side of the ultrasonic oscillator array perpendicular to a circular-arc surface resulting from the arrangement of the plurality of ultrasonic oscillators and electrically connected to the plurality of ultrasonic oscillators, respectively; a backing material layer that is disposed on a back surface of the ultrasonic oscillator array serving as an inside with respect to an arrangement surface of the plurality of ultrasonic oscillators, has an outer surface having a circular-arc cross section, and is provided with a recess on the inside opposite to the outer surface; a wiring board having a plurality of wiring lines electrically connected to the plurality of electrodes of the electrode part; and a cable wiring part in which a plurality of cables connected to the plurality of wiring lines, respectively, are wiring-connected. At least a portion of the cable wiring part is included in the recess of the backing material layer.

Here, it is preferable that the backing material layer has a bow shape, a semicylindrical shape, a shape obtained by cutting a column with a plane parallel to a centerline, or a semicircular columnar shape, and a bottom surface of the backing material layer is one continuous plane located on the same plane or two separated planes located on the same plane.

Additionally, it is preferable that the recess of the backing material layer is provided from an outer side surface of the backing material layer toward a center side thereof.

Additionally, it is preferable that the recess of the backing material layer is either a through-hole penetrating from one outer side surface of the backing material layer to the other outer side surface thereof, or a counterbore recessed from at least one outer side surface of the backing material layer toward the center side thereof.

Additionally, it is preferable that the through-hole has a circular shape, a shape hollowed out in a polygonal shape, or semicircular shape, the counterbore is formed by performing counterboring from at least one outer side surface of the backing material layer toward the center side thereof, and the counterbore is a bow-shaped counterbore, a semicircular counterbore, a polygonal counterbore, a pyramidal counterbore, or a conical counterbore.

Additionally, it is preferable that the recess of the backing material layer is formed so as to enlarge in a direction away from the ultrasonic oscillator array.

Additionally, it is preferable that the cable wiring parts are respectively disposed on both outer side surfaces of the backing material layer, and the recesses of the backing material layer are provided on both the outer side surfaces of the backing material layer or the recess of the backing material layer is provided by penetrating both the outer side surfaces in order to dispose the respective cable wiring parts.

Additionally, it is preferable that the cable wiring part is provided on a surface of the wiring board on the center side of the backing material layer.

Additionally, it is preferable that a gap of the recess between the cable wiring part housed in the recess of the backing material layer and the backing material layer is filled with a filler.

Additionally, it is preferable that at least a portion of the cable wiring part is covered with the filler.

Additionally, it is preferable that the ultrasonic oscillator unit further comprises a cable unit that includes the wiring board and the cable wiring part and is formed by connecting the plurality of wiring lines of the wiring board and the plurality of cables wiring-connected to the cable wiring part, respectively, to each other.

Additionally, it is preferable that the cable unit is a multilayer interconnection board having a flexible printed wiring board that is the wiring board, and a rigid printed wiring circuit board having the cable wiring part.

Additionally, it is preferable that the wiring board has a flexible printed wiring board, a printed wiring circuit board, or both the boards.

Additionally, it is preferable that the flexible printed wiring board is electrically connected to the electrode part by heat fusion and is disposed on the outer side surface of the ultrasonic oscillator array.

Additionally, it is preferable that the flexible printed wiring board is electrically connected to the electrode part using an anisotropic conductive sheet or anisotropic conductive paste and is disposed on an outer side surface of the ultrasonic oscillator array.

Additionally, it is preferable that the flexible printed wiring board is disposed on an outer side surface of the ultrasonic oscillator array, and a filler is injected into a gap of the recess of the backing material layer, in which the cable wiring part is housed, to fill the gap.

Additionally, in order to achieve the above object, an ultrasonic endoscope of the invention is an ultrasonic endoscope for imaging an inside of a body cavity of a subject to acquire an ultrasound image and an endoscopic image, respectively. The ultrasonic endoscope comprises an insertion part to be inserted into the body cavity; an ultrasonic observation part that is provided at a distal end of the insertion part, includes the above ultrasonic oscillator unit, and acquires the ultrasound image; an endoscope observation part that is provided closer to a proximal end side than the ultrasonic observation part in the insertion part and includes an illumination optical system that emits illumination light that illuminates a region to be imaged within the body cavity, and an imaging optical system that images the region to be imaged that is illuminated with the illumination light from the illumination optical system; and a treatment tool channel that is provided closer to a proximal end side than the ultrasonic observation part in the insertion part and includes a treatment tool delivery port for inserting a treatment tool into the body cavity.

According to the invention, it is possible to provide the ultrasonic oscillator unit that can be small-sized, has excellent workability in a case where the respective electrodes of the ultrasonic oscillator array and numerous cables are wired, has low difficulty of an operation step, has a wiring structure in which a load on a cable is unlikely to occur and there is less risk of disconnection, and is suitable for use in the ultrasonic endoscope, and the ultrasonic endoscope using the same.

According to the invention, it is possible to provide the ultrasonic oscillator unit that is capable of inspecting the ultrasonic oscillator array before cable wiring, has high manufacture stability, and does not cause an increase in cost, and is suitable for use in the ultrasonic endoscope, and ultrasonic endoscope using the same, in addition to the above effects.

DESCRIPTION OF THE PREFERRED EMBODIMENTS

An ultrasonic oscillator unit related to the invention and an ultrasonic endoscope using the ultrasonic oscillator unit will be described below in detail on the basis of preferred embodiments illustrated in the accompanying drawings.

Figure 1:
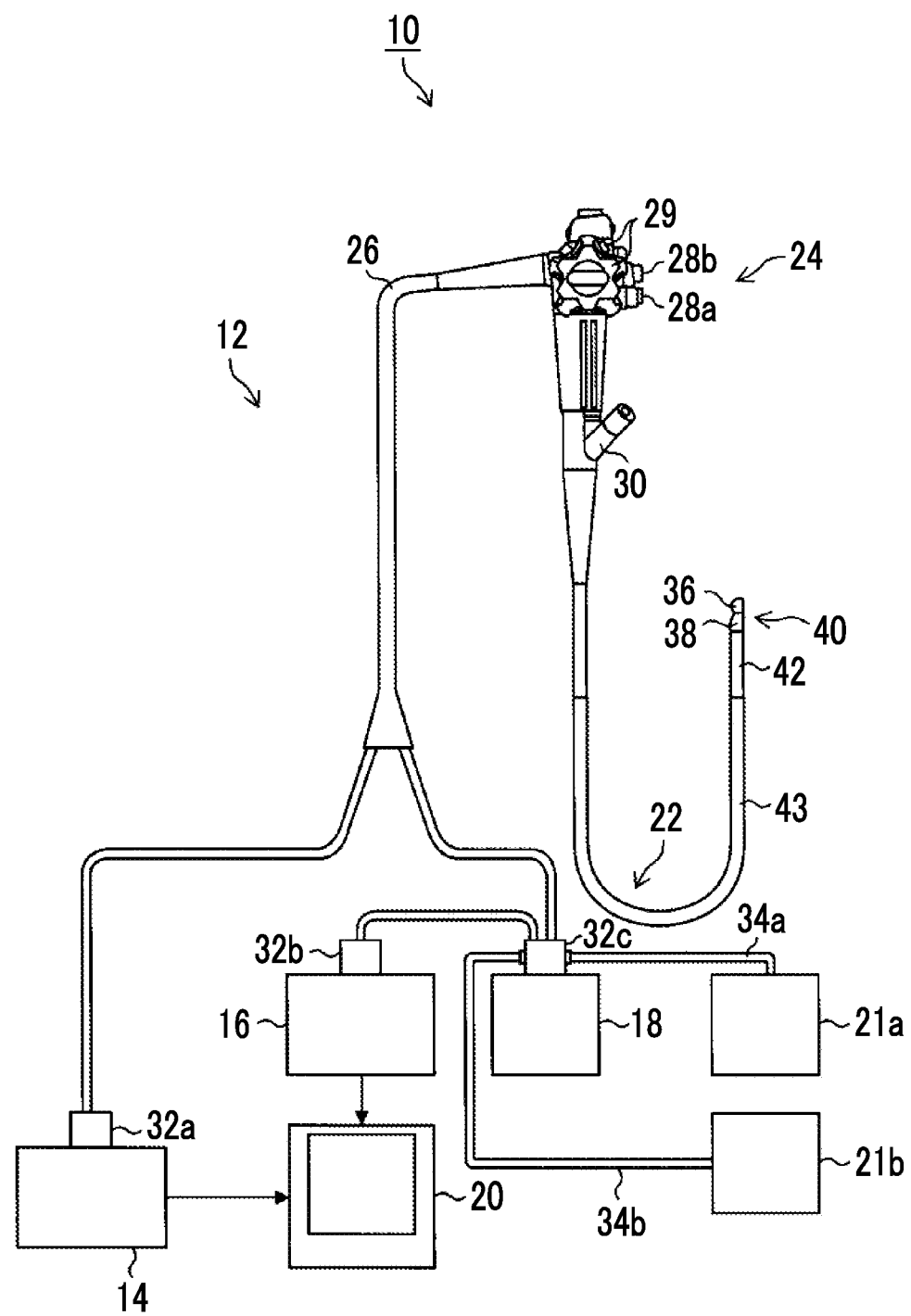
FIG. 1 is a schematic configuration view illustrating an example of the configuration of an ultrasonic inspection system using an ultrasonic endoscope to which an ultrasonic oscillator unit of the invention is applied.

FIG. 1 is a schematic configuration view illustrating an example of the configuration of an ultrasonic inspection system using the ultrasonic endoscope of the invention using the ultrasonic oscillator unit of the invention.

An ultrasonic inspection system 10 illustrated in FIG. 1 allows observation of the gallbladder or the pancreas that is difficult in the ultrasonic inspection from the body surface of a subject, such as a patient, via alimentary canals, such as the esophagus, the stomach, the duodenum, the small intestine, and the large intestine that are body cavities of the subject, includes the ultrasonic oscillator unit of the invention, and acquires an ultrasound image of a region to be observed of the subject while inserting the ultrasonic endoscope of the invention having an ultrasonic observation part and an endoscope observation part into the body cavities of the subject to observe an endoscopic image of the subject. The ultrasonic observation part acquires an ultrasonic tomographic image (hereinafter referred to as the ultrasound image), and the endoscope observation part acquires an endoscopic optical image (hereinafter referred to as the endoscopic image).

As illustrated in FIG. 1, the ultrasonic inspection system 10 is configured to include an ultrasonic endoscope 12 of the invention using an ultrasonic oscillator unit (46: refer to FIGS. 2 to 5) of the invention, an ultrasonic wave processor device 14 that creates the ultrasound image, an endoscope processor device 16 that creates the endoscopic image, a light source device 18 that supplies the illumination light for illuminating the inside of a body cavity to the ultrasonic endoscope 12, and a monitor 20 that displays the ultrasound image and/or the endoscopic image.

Additionally, the ultrasonic inspection system 10 further includes a water supply tank 21a that stores washing water or the like, and a suction pump 21b that suctions a suction object (including the supplied washing water) within the body cavity. In addition, although not illustrated, the ultrasonic inspection system 10 may further include a supply pump that supplies washing water within the water supply tank 21a or gas, such as external air, to a pipe line (not illustrated) within the ultrasonic endoscope 12.

First, the ultrasonic endoscope 12 of the invention has an ultrasonic observation part 36 and an endoscope observation part 38, which are constituted of the ultrasonic oscillator unit (46: refer to FIGS. 2 to 5) of the invention, at a distal end thereof, and images the inside of the body cavity of the subject to acquire the ultrasound image (echo signals) and the endoscopic image (image signals), respectively.

The ultrasonic endoscope 12 includes the ultrasonic observation part 36 and the endoscope observation part 38 at the distal end thereof, and is constituted of an insertion part 22 for being inserted into the body cavity of the subject, an operating part 24 that is provided continuously with a proximal end part of the insertion part 22 to allow an operator, such as a doctor or an engineer to perform an operation, and a universal cord 26 has one end connected to the operating part 24.

An air/water supply button 28a that opens and closes an air/water supply pipe line (not illustrated) from the water supply tank 21a and a suction button 28b that open and close a suction pipe line (not illustrated) from the suction pump 21b are provided side by side at the operating part 24, and the operating part 24 is provided with a pair of angle knobs 29 and 29 and a treatment tool insertion port (also referred to as a forceps port) 30.

Here, the water supply tank 21a is a tank for storing the washing water to be supplied to the air/water supply pipe line within the ultrasonic endoscope 12 for washing the endoscope observation part 38 and the like of the ultrasonic endoscope 12. In addition, the air/water supply button 28a is used to jet gas, such as air, and water, such as washing water, which has been supplied through the air/water supply pipe line from the water supply tank 21a, from the endoscope observation part 38 on a distal end side of the insertion part 22.

Additionally, the suction pump 21b suctions the suction pipe line (not illustrated) in order to suction the suction object within the body cavity (including the supplied washing water) from the distal end side of the ultrasonic endoscope 12. The suction button 28b is used to suction the suction object within the body cavity from the distal end side of the insertion part 22 with a suction force of the suction pump 21b.

Additionally, the forceps port 30 is a port for allowing a treatment tool, such as forceps, a puncturing needle, or a high-frequency knife to be inserted therethrough.

The other end part of the universal cord 26 is provided with an ultrasonic wave connector 32a connected to the ultrasonic wave processor device 14, an endoscope connector 32b connected to the endoscope processor device 16, and a light source connector 32c connected to the light source device 18. The ultrasonic endoscope 12 is attachably and detachably connected to the ultrasonic wave processor device 14, the endoscope processor device 16, and the light source device 18 via the connectors 32a, 32b, and 32c, respectively. Additionally, an air/water supply tube 34a to which the water supply tank 21a is to be connected, a suction tube 34b to which the suction pump 21b is to be connected, and the like are connected to the light source connector 32c.

The insertion part 22 is constituted of the distal end part (distal end rigid part) 40 that is formed of a rigid member and has the ultrasonic observation part 36 and the endoscope observation part 38, a bending part 42 that is provided continuously with a proximal end side of the distal end part 40, is formed by coupling a plurality of bendable pieces to each other, and is bendable, and a flexible part 43 that couples a proximal end side of the bending part 42 and a distal end side of the operating part 24 to each other and is thin, elongated, and flexible, sequentially from the distal end side.

The bending part 42 is remotely bending-operated by rotationally moving the pair of angle knobs 29 and 29 provided at the operating part 24. Accordingly, the distal end part 40 can be directed to a desired direction.

Additionally, a balloon into which an ultrasonic transmission medium (for example, water, oil, or the like) for covering the ultrasonic observation part 36 is injected may be attachably and detachably mounted on the distal end part 40. Since ultrasonic waves and the echo signals are significantly dampened in the air, the ultrasonic transmission medium is injected into the balloon to expand the balloon and is made to abut against the region to be observed. Accordingly, air can be eliminated from between an ultrasonic oscillator (ultrasonic transducer) array (50: refer to FIGS. 2 to 5) of the ultrasonic observation part 36 and the region to be observed, and the damping of the ultrasonic waves and the echo signals can be prevented.

In addition, the ultrasonic wave processor device 14 is a device for creating and supplying ultrasonic signals (data) for generating the ultrasonic waves in the ultrasonic oscillator array (50: refer to FIGS. 2 to 5) of the ultrasonic oscillator unit (46) of the ultrasonic observation part 36 of the distal end part 40 of the insertion part 22 of the ultrasonic endoscope 12. Additionally, the ultrasonic wave processor device 14 is a device for receiving and acquiring the echo signals (data), which is reflected from the region to be observed to which the ultrasonic waves are radiated, with the ultrasonic oscillator array (50), and creating the ultrasound image that is obtained by performing various kinds of signal (data) processing on the acquired echo signals and is displayed on the monitor 20.

The endoscope processor device 16 is a device for receiving and acquiring captured image signals (data) acquired from the region to be observed illuminated with the illumination light from the light source device 18 in the endoscope observation part 38 of the distal end part 40 of the insertion part 22 of the ultrasonic endoscope 12, and creating the endoscopic image that is obtained by performing various kinds of signal (data) processing and image processing on the acquired image signals and is displayed on the monitor 20.

In addition, the processor devices 14 and 16 may be constituted of processors, such as a personal computer (PC).

In order to image the region to be observed within the body cavity to acquire the image signals with the endoscope observation part 38 of the ultrasonic endoscope 12, the light source device 18 is a device for generating illumination light, such as white light consisting of three primary color lights, such as red light (R), green light (G), and blue light (B), or specific wavelength light to supply the illumination light to the ultrasonic endoscope 12 to propagate the illumination light with a light guide or the like within the ultrasonic endoscope 12 (not illustrated), and emitting the illumination light from the endoscope observation part 38 of the distal end part 40 of the insertion part 22 of the ultrasonic endoscope 12 for illuminating the region to be observed within the body cavity with the illumination light.

The monitor 20 receives respective video signals created by the ultrasonic wave processor device 14 and the endoscope processor device 16 to display the ultrasound image and the endoscopic image. As for the display of the ultrasound image and the endoscopic image, it is possible to appropriately display one of the images on the monitor 20 through switching and to simultaneously display both the images. In addition, a monitor for displaying the ultrasound image and a monitor for displaying the endoscopic image may be separately provided, or the ultrasound image and the endoscopic image may be displayed in other arbitrary forms.

Next, the configuration of the distal end part of the insertion part of the ultrasonic endoscope will be described in detail with reference to FIGS. 2 to 4.

Figure 2:
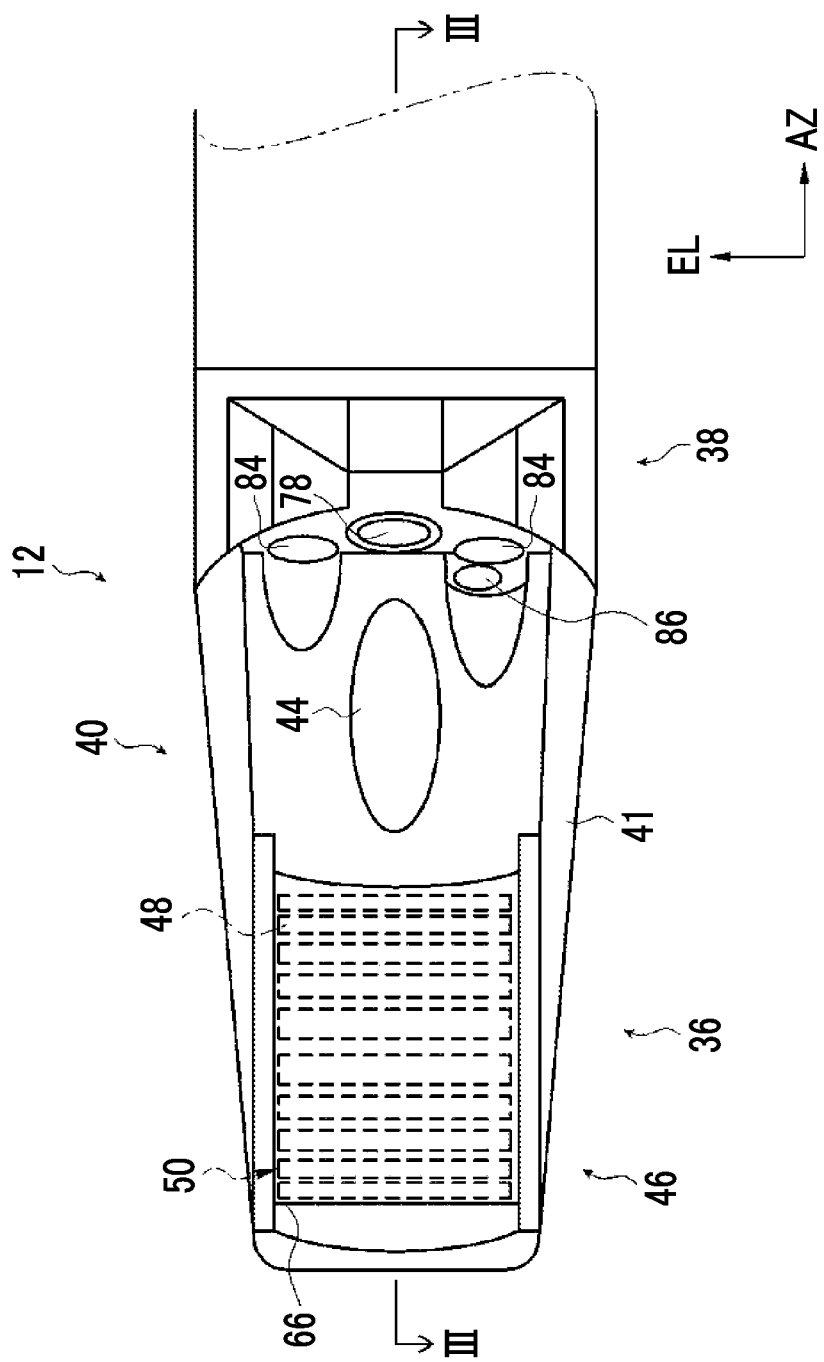
FIG. 2 is a partially enlarged plan view illustrating a distal end part of the ultrasonic endoscope illustrated in FIG. 1.

FIG. 2 is a partially enlarged plan view illustrating the distal end part of the ultrasonic endoscope illustrated in FIG. 1 and its vicinity. FIG. 3 is a view taken along line illustrated in FIG. 2 and seen from an arrow direction and is a longitudinal sectional view of the distal end part of the ultrasonic endoscope illustrated in FIG. 2 cut along a centerline in a longitudinal direction thereof. FIG. 4 is a partially enlarged longitudinal cross-sectional view of the ultrasonic observation part of the distal end part of the ultrasonic endoscope illustrated in FIG. 3. FIG. 5 is a view taken along line V-V illustrated in FIG. 2 and seen from an arrow direction and is a cross-sectional view cut along a centerline of a circular-arc structure of the ultrasonic oscillator array of the ultrasonic observation part of the distal end part of the ultrasonic endoscope illustrated in FIG. 2.

Figure 3:
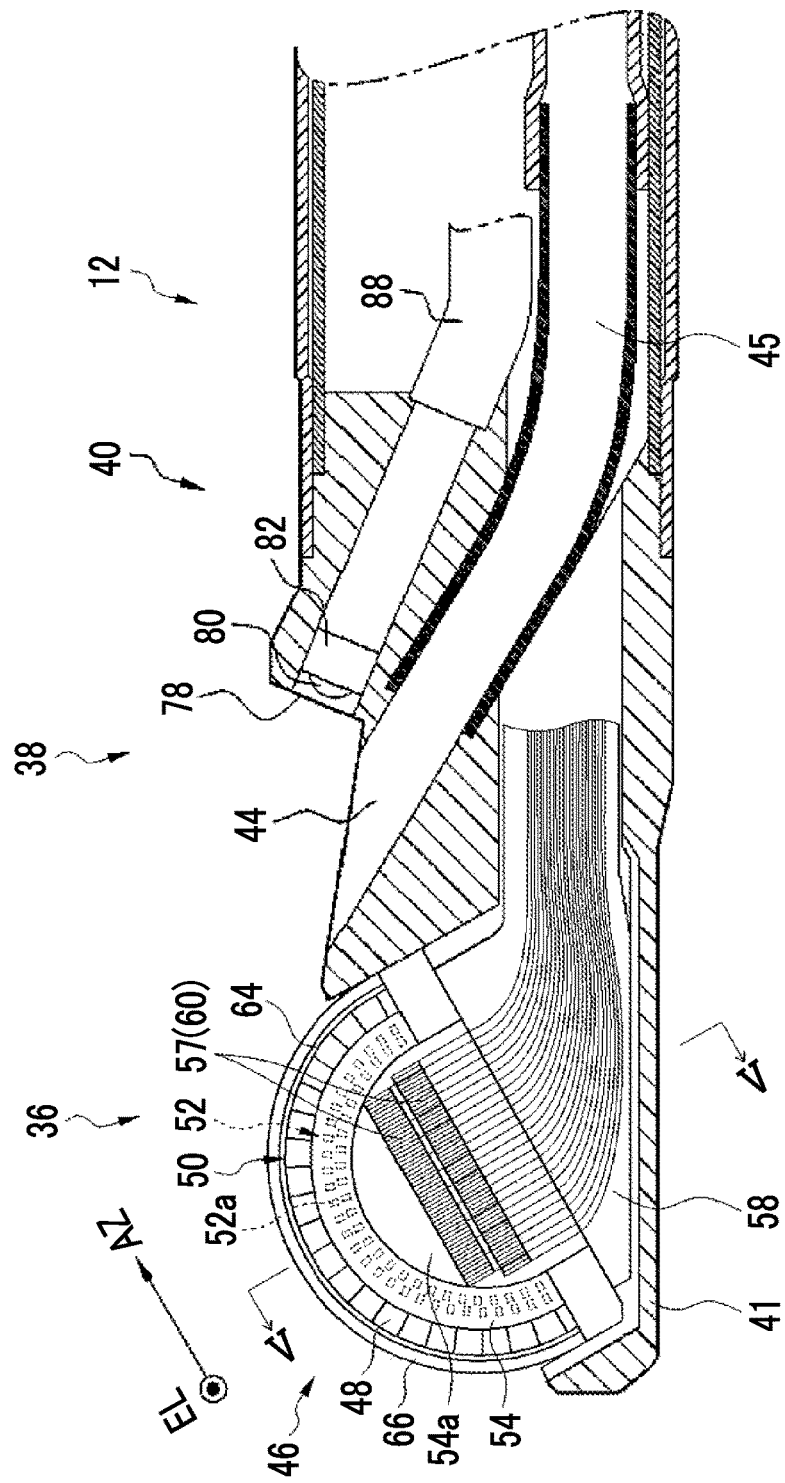
FIG. 3 is a view taken along line illustrated in FIG. 2 and seen from an arrow direction and is a partially longitudinal cross-sectional view of the distal end part of the ultrasonic endoscope illustrated in FIG. 2.

As illustrated in FIGS. 2 and 3, the distal end part 40 of the ultrasonic endoscope 12 is provided with the ultrasonic observation part 36 on a distal end side thereof for acquiring the ultrasound image, the endoscope observation part 38 on a proximal end side thereof for acquiring the endoscopic image, and a treatment tool delivery port 44 therebetween, and these are altogether attached to and held by a sheathing member 41 that serves as a distal end part body of the distal end part 40 of the ultrasonic endoscope 12 and is made of a rigid member, such as a hard resin.

In the example illustrated in FIG. 2, although the treatment tool delivery port 44 is provided between the ultrasonic observation part 36 and the endoscope observation part 38, the invention is not particularly limited to the illustrated example. The treatment tool delivery port 44 may be provided within the endoscope observation part 38 or may be provided closer to the proximal end side (bending part 42 side) than the endoscope observation part 38.

Figure 4:
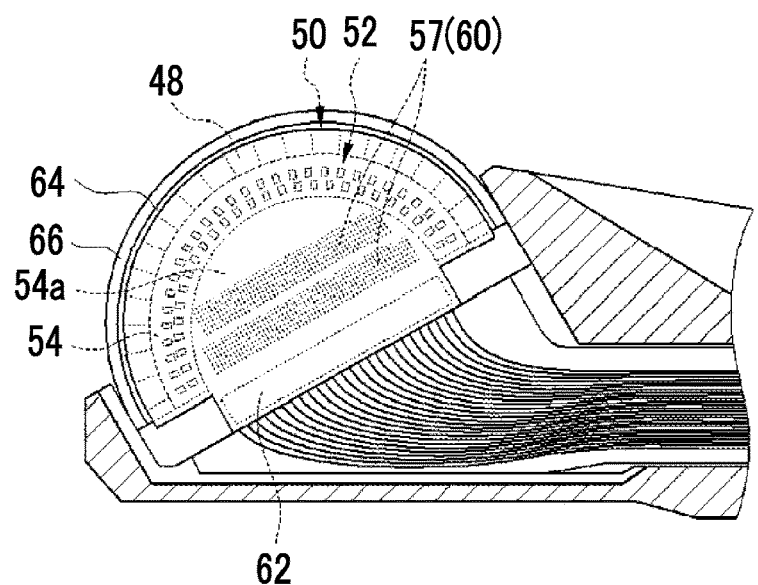
FIG. 4 is a partially enlarged cross-sectional view of an ultrasonic observation part of the distal end part of the ultrasonic endoscope illustrated in FIG. 2.
Figure 5:
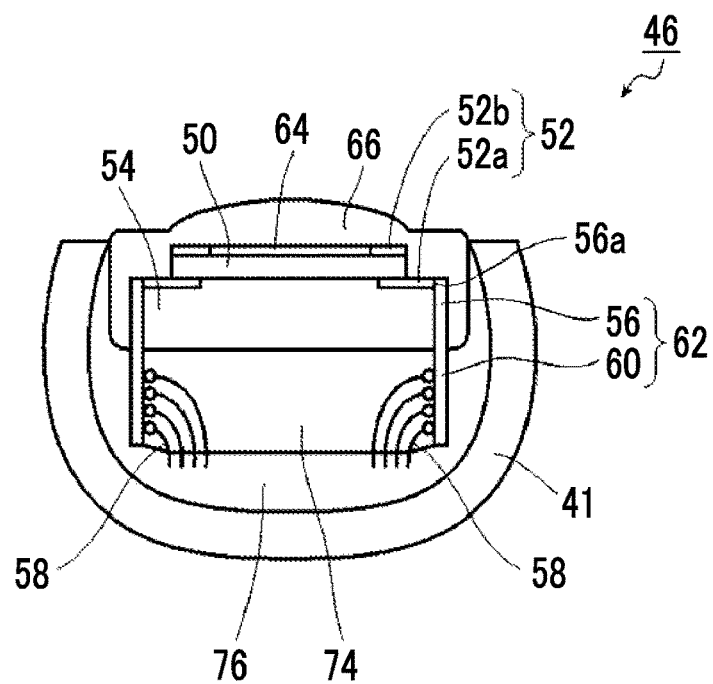
FIG. 5 is a view taken along line V-V illustrated in FIG. 3 and seen from an arrow direction and is a cross-sectional view of an example of the ultrasonic observation part of the distal end part of the ultrasonic endoscope illustrated in FIG. 3.

As illustrated in FIGS. 2 to 4, the ultrasonic observation part 36 is constituted of the ultrasonic oscillator unit 46 of the invention and the sheathing member 41 for attaching and holding the ultrasonic oscillator unit 46.

The ultrasonic oscillator unit 46 has the ultrasonic oscillator array 50 including a plurality of ultrasonic oscillators (transducers) 48, an electrode part 52 provided on an outer side surface of the ultrasonic oscillator array 50, a backing material layer 54 that supports the respective ultrasonic oscillators 48 of the ultrasonic oscillator array 50 from lower surface sides thereof, a flexible printed wiring board (hereinafter simply referred to as a flexible printed circuit (FPC)) 56 connected electrically to the electrode part 52, and a cable wiring part 60 to which a plurality of cables 58 connected to the FPC 56 are wiring-connected. Here, in the illustrated example, the FPC 56 and the cable wiring part 60 are integrated as a cable unit 62.

Additionally, the ultrasonic oscillator unit 46 further has an acoustic matching layer 64 laminated on the ultrasonic oscillator array 50 and the acoustic lens 66 laminated on the acoustic matching layer 64. That is, the ultrasonic oscillator unit 46 includes a laminated body of the acoustic lens 66, the acoustic matching layer 64, the ultrasonic oscillator array 50, and the backing material layer 54.

The acoustic matching layer 64 is a layer for matching the acoustic impedance between a subject, such as a human body, and the ultrasonic oscillators 48.

The acoustic lens 66 attached on the acoustic matching layer 64 is a lens for condensing the ultrasonic waves emitted from the ultrasonic oscillator array 50 toward the region to be observed. The acoustic lens 66 is made of, for example, silicon-based resin (millable type silicone rubber (HTV rubber), liquid silicone rubber (RTV rubber), or the like), butadiene-based resin, polyurethane-based resin, or the like. In order for the acoustic matching layer 64 to match the acoustic impedance between the subject and the ultrasonic oscillators 48 and increase the transmittance of the ultrasonic waves, powder, such as titanium oxide, alumina, or silica, is mixed with the acoustic lens 66 as needed.

The ultrasonic oscillator array 50 is a 48-to-192 channel (CH) array including a plurality of, for example, 48 to 192 rectangular parallelepiped-shaped ultrasonic oscillators (transducers) 48 that are arranged outward in a circular-arc shape.

That is, the ultrasonic oscillator array 50 is an array in which a plurality of ultrasonic oscillators 48 are arranged at a predetermined pitch in a one-dimensional array as in the illustrated example as an example. In this way, the respective ultrasonic oscillators 48 that constitute the ultrasonic oscillator array 50 are arranged at equal intervals in a convexly curved shape in an axis direction (the longitudinal axis direction of the insertion part 22) of the distal end part 40 and are sequentially driven on the basis of driving signals input from the ultrasonic wave processor device 14. Accordingly, convex electronic scanning is performed using a range where the ultrasonic oscillators 48 illustrated in FIG. 2 are arranged, as a scanning range.

The ultrasonic oscillator array 50 is arranged such that the length of the ultrasonic oscillators 48 in a longitudinal direction (EL (elevation) direction) orthogonal to an AZ direction (AZ (azimuth) direction) is shorter than that in a direction parallel to a bottom surface 54d of the backing material layer 54 and a rear end side thereof is inclined so as to overhang. As illustrated in FIG. 5, each ultrasonic oscillator 48 has a configuration in which electrodes are formed on both surfaces of, for example, a thick film of a piezoelectric body, such as PZT (lead zirconium titanate) or PVDF (polyvinylidene fluoride). One electrode is an individual electrode 52a that is separately independent for each ultrasonic oscillator 48, and the other electrode is a common electrode (for example, grand (touch-down) electrode) 52b common to all the ultrasonic oscillators 48. In the illustrated example, a plurality of the individual electrodes 52a extends lower surfaces of end parts of the plurality of ultrasonic oscillators 48 to an outer surface (top surface) 54b of the backing material layer 54 that serves as an arrangement surface, and the common electrode 52b is provided on upper surfaces of the end parts of the ultrasonic oscillators 48. The plurality of individual electrodes 52a and the common electrode 52b constitute the electrode part 52.

In addition, although illustration is omitted, a gap between two adjacent ultrasonic oscillator 48 is filled with a filler material, such as epoxy resin.

In the ultrasonic oscillator unit 46 of the ultrasonic observation part 36, in a case where each ultrasonic oscillator 48 of the ultrasonic oscillator array 50 is driven and a voltage is applied to both the electrodes of the ultrasonic oscillator 48, the piezoelectric bodies oscillate to sequentially driving generate the ultrasonic waves, and the ultrasonic waves are radiated toward the region to be observed of the subject. Then, by sequentially the plurality of ultrasonic oscillators 48 with an electronic switch, such as a multiplexer, scanning is performed with the ultrasonic waves within a scanning range along a curved surface on which the ultrasonic oscillator array 50 is disposed, for example, within a range of about several tens of mm from the center of curvature of the curved surface.

Additionally, in a case where the echo signals (ultrasonic echoes) reflected from the region to be observed are received, the piezoelectric bodies oscillate to generate voltages, and the voltages are output to the ultrasonic wave processor device 14 as electrical signals (ultrasonic detection signals) according to the received ultrasonic echoes. After various kinds of signal processing are performed in the ultrasonic wave processor device 14, the ultrasound image is displayed on the monitor 20.

As illustrated in FIGS. 3 and 4, the electrode part 52 is provided in a circular-arc shape on an end surface side (of the respective ultrasonic oscillators 48) of the ultrasonic oscillator array 50 perpendicular to a circular-arc surface resulting from the arrangement of the plurality of (48 to 192) ultrasonic oscillators 48, and includes the plurality of (48 to 192) electrodes 52a conducted to the plurality of (48 to 192) ultrasonic oscillators 48, respectively. In addition, the common electrode of the plurality of ultrasonic oscillators 48 may be included in the electrode part 52. In the invention, the "perpendicular" is not necessarily limited to 90 degrees, and includes substantially perpendicular, for example, 95 degrees±5 degrees, that is, an angle within a range of 85 degrees to 90 degrees.

In addition, in FIGS. 3 and 4, the plurality of electrodes 52a arranged in a circular-arc shape and the electrode part 52 including these electrodes are hidden under the backing material layer 54 and are not visible, but are indicated by dashed lines for easy understanding.

The electrode part 52 is provided on the outer side surface of the ultrasonic oscillator array 50 perpendicular to the arrangement surface of the ultrasonic oscillators 48. However, in a case where the number of ultrasonic oscillators 48 is small, the electrode part 52 may be provided on one outer side surface. However, it is preferable that the number of ultrasonic oscillators 48 is larger. Thus, it is preferable that the plurality of electrodes 52a are provided on both the outer side surfaces of the ultrasonic oscillator array 50.

In addition, in the example illustrated in FIG. 5, the plurality of electrodes 52a are constituted of the individual electrodes provided on the end surface sides of the respective ultrasonic oscillators 48 in their longitudinal direction. However, the invention is not limited to this. As long as the individual electrodes 52a of the ultrasonic oscillators 48 are electrically connected, the individual electrodes 52a may be constituted of separate electrodes connected by wiring lines from the individual electrodes. Additionally, although the common electrode is directly included in the electrode part 52, an electrode connected by a wiring line from the common electrode 52b may be included.

It is preferable that the plurality of electrodes 52a and the common electrode 52b of the electrode part 52 are provided as electrode pads.

Figure 6:
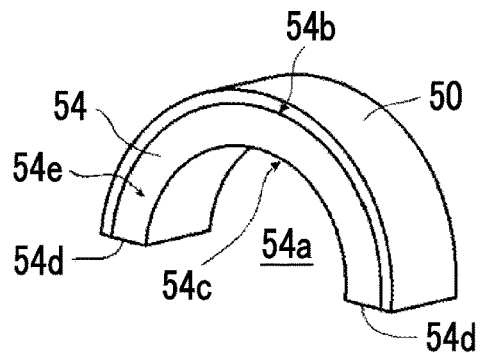
FIG. 6 is a perspective view illustrating an example of the structure of the backing material layer of the ultrasonic oscillator unit of the ultrasonic observation part illustrated in FIG. 4.

Next, as illustrated in FIGS. 3 and 6, the backing material layer 54 is a layer of a member that is made of a backing material disposed on an inside with respect to the arrangement surface of the plurality of ultrasonic oscillators 48, that is, a back surface (lower surface) of the ultrasonic oscillator array 50. The backing material layer 54 has a top surface (upper surface) 54b formed in a convex circular-arc shape in cross-section and has a lower surface 54c formed in a concave circular-arc shape in section, and accordingly, is made of a semicylindrical backing material having the outer surface 54b having the circular-arc cross-section and including a recess on the inside opposite to the outer surface 54b, preferably, a semicircular columnar recess 54a penetrating from one outer side surface of the backing material layer 54 to the other outer side surface thereof in the illustrated example, that is, having a recess 54a having a circular-arc cross-section on a lower surface side. Hence, it is preferable that the bottom surface 54d (inner surface) of the backing material layer 54 includes two separated planes that are located on the same plane as in the illustrated example.

Here, in the example illustrated in FIGS. 3 and 6, the backing material layer 54 has a semicylindrical shape. However, the invention is not limited to this. The backing material layer 54 may have a semicircular columnar shape as in backing material layers 68, 69, and 70 illustrated in FIGS. 7, 8, and 9. In this case, it is preferable that bottom surfaces 68c, 69c, and 70c of the backing material layers 68, 69, and 70 include one continuous plane located on the same plane. In addition, in FIGS. 6 to 9, for the sake of description, constituent elements other than the ultrasonic oscillator array and the backing material layer among the constituent elements of the ultrasonic oscillator unit of the invention are omitted.

Moreover, preferably, the backing material layer used for the invention may have a bow shape (a partial cylindrical shape having a circular arc smaller than a semicircle), may have a shape obtained by cutting a column with a plane parallel to a centerline, or may have a shape including a through recess, such as a semi-elliptical shape, a polygonal shape, or an abnormal shape, which opens from a bottom surface side of the backing material layer having a semicircular columnar shape or the shape obtained by cutting the column with the plane parallel to the centerline and penetrates from one outer side surface of the backing material layer to the other outer side surface thereof.

Additionally, the backing material layer 54 of the illustrated example has the recess 54a that can include at least a portion of the cable wiring part 60. In the illustrated example, the recess 54a is a semicircular columnar recess (first recess) penetrating from one outer side surface of the backing material layer 54 to the other outer side surface thereof. However, the invention is not limited to this, and any kind of recess may be adopted as long as the recess can house at least a portion of the cable wiring part 60.

For example, it is preferable that the recess of the backing material layer used for the invention is provided from the outer side surfaces of the backing material layer toward a center side of the backing material layer. Hence, it is more preferable that the recess is the recess (the first recess of the invention) penetrating from one outer side surface of the backing material layer to the other outer side surface thereof or a recess (a second recess of the invention) recessed from at least one outer side surface of the backing material layer toward the center side thereof.

Here, the first recess may be a recess (first recess) that is circularly hollowed out from the bottom surface side of the backing material layer and penetrates from one outer side surface of the backing material layer to the other outer side surface thereof, and may be a through recess, such as the above-described semi-elliptical shape, polygonal shape, or an abnormal shape.

Figure 7:
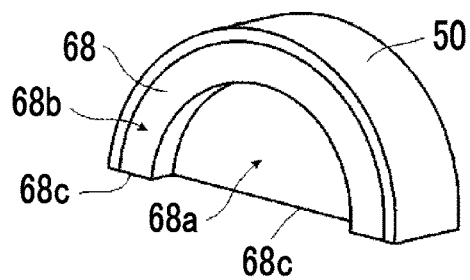
FIG. 7 is a perspective view illustrating another example of the structure of the backing material layer of the ultrasonic oscillator unit of the invention.
Figure 8:
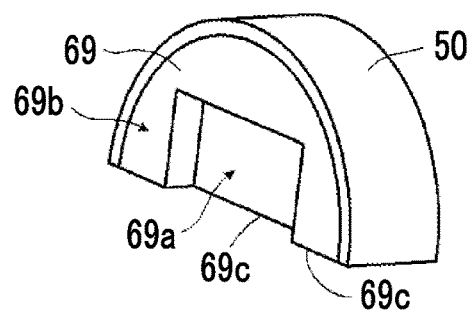
FIG. 8 is a perspective view illustrating still another example of the structure of the backing material layer of the ultrasonic oscillator unit of the invention.
Figure 9:
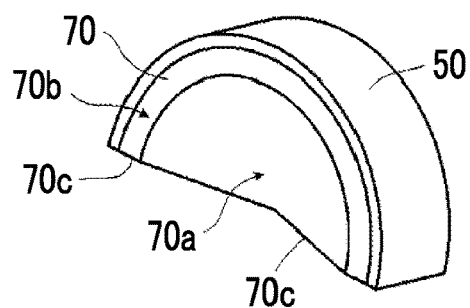
FIG. 9 is a perspective view illustrating a still further example of the structure of the backing material layer of the ultrasonic oscillator unit of the invention.

Meanwhile, the second recess may be a counterbore formed by performing counterboring from at least one outer side surface of the backing material layer toward the center side thereof, for example, a semicircular counterbore 68*a*, a quadrangular counterbore 69*a*, and a conical counterbore 70*a* respectively formed in the semicircular columnar backing material layers 68, 69, and 70 on one-side outer side surfaces 68*b*, 69*b*, and 70*b* illustrated in FIGS. 7, 8, and 9, or may be a bow-shaped counterbore, a polygonal counterbore, a pyramidal counterbore, or the like, though not illustrated. Additionally, even in a case where the recess is not above-described counterbore, a recess formed in advance in the backing material layer may be adopted as long as the recess is provided from the outer side surfaces of the backing material layer toward the center side thereof.

It is preferable such a recess is formed so as enlarge in a direction away from the ultrasonic oscillator array 50, for example, like the conical counterbore 70*a*.

Moreover, in a case where recesses used in the invention do not penetrate like the counterbores 68*a*, 69*a*, and 70*a*, it is preferable that the recesses are provided on both the outer side surfaces, that is, both side surfaces of the backing material layer.

The backing material that constitutes the backing material layer 54 functions as a cushioning material that flexibly supports the respective ultrasonic oscillators 48 and the like of the ultrasonic oscillator array 50. For this reason, the backing material includes a material having rigidity, such as hard rubber, and an ultrasonic damping material (ferrite, ceramics, or the like) is added to the backing material as needed.

Hence, the ultrasonic oscillator array 50 is an array in which, in the illustrated example, the plurality of rectangular parallelepiped-shaped ultrasonic oscillators 48 are parallel to the longitudinal direction thereof, preferably, are arranged at equal intervals, on the circular-arc outer surface 54*b* used as an upper surface of the backing material layer 54 formed in a circular-arc shape in cross-section, that is, an array in which the plurality of ultrasonic oscillators 48 are arranged outward in a circular-arc shape.

The FPC 56 is a wiring board used in the invention, and has a plurality of (48 to 192) wiring lines for being respectively electrically connected to the plurality of (48 to 192) electrodes 52*a* of the electrode part 52 as illustrated in FIGS. 3 and 4. That is, in the illustrated example, the FPC 56 has a plurality of (48 to 192) wiring pads 56*a* for being respectively electrically connected to the plurality of electrodes 52*a* (electrode pads) of the electrode part 52, a plurality of (48 to 192) wiring pads 57 for being respectively connected to the cable wiring part 60 to which the plurality of (48 to 192) cables 58 are wiring-connected, and a plurality of wiring lines (not illustrated) for connecting the plurality of wiring pads 56*a* and the plurality of wiring pads 57 to each other, respectively.

The cable wiring part 60 is a cable wiring part in which the plurality of (48 to 192) of cables 58 respectively connected to the plurality of (48 to 192) wiring lines of the FPC 56 are wiring-connected in advance.

In the example illustrated in FIG. 5, the cable wiring part 60 shares the plurality of wiring pads 57 of the FPC 56, and the plurality of (48 to 192) cables 58 are wiring-connected to the plurality of (48 to 192) wiring pads 57, respectively, in advance.

In addition, in the example illustrated in FIG. 5, the FPC 56 and the cable wiring part 60 are constituted as the integrated cable unit 62.

Here, as the cable unit 62, one wiring board, for example, a multilayer board in which a flexible wiring board, such as the FPC 56, and a rigid wiring board, such as a printed wiring board (hereinafter referred to as a printed circuit board (PCB)) or a printed wiring board (hereinafter referred to as a printed wired board (PWB)), are integrated with each other is used. In the cable unit 62, the plurality of wiring pads 57 of the FPC 56 are provided on the rigid wiring board, the plurality of cables 58 are wiring-connected to the plurality of wiring pads 57 in advance so as to provide the cable wiring part 60, and the ultrasonic oscillator array 50 and the FPC 56 of the cable unit 62 are pasted to each other so as to electrically connect the plurality of wiring pads 56*a* and the plurality of electrodes 52*a* (electrode pad) to each other such that the plurality of wiring pads 56*a* of the FPC 56 respectively electrically connected to the plurality of wiring pads 57 and a the plurality of electrodes 52*a* (electrode pads) of the electrode part 52 of the ultrasonic oscillator array 50 come into contact with each other.

Here, the pasting (that is, electrical connection) between the plurality of wiring pads 56*a* of the FPC 56 and the plurality of electrodes 52*a* (electrode pads) of the electrode part 52 of the ultrasonic oscillator array 50 is preferably performed using an anisotropic conductive sheet or an anisotropic conductive paste and is preferably performed by heat fusion. In addition, the electrical connection between the wiring pads 56*a* and the electrodes 52*a* is not necessarily limited to these connection methods, and any kind of method may be performed using as long as the workability of wiring is not hindered and the difficulty of the operation step does not become high, and well-known methods, such as wire bonding and soldering, may be used.

In this way, in the invention, it is possible to provide the ultrasonic oscillator unit that can simplify ultrasonic oscillator wiring work, improve efficiency and improve workability, can be small-sized, has excellent workability in a case where the respective electrodes of the ultrasonic oscillator array and numerous cables are wired and low difficulty of the operation step, has a wiring structure in which a load on a cable is unlikely to occur and there is less risk of disconnection, and is suitable for use in the ultrasonic endoscope.

In the above-described example, the FPC 56 and the cable wiring part 60 are constituted as the integrated cable unit 62. However, the invention may not be limited to this, and the FPC 56 and the cable wiring part 60 may not be integrated and may be constituted as separate members. That is, the FPC 56 may have the above configuration and have the plurality of (48 to 192) wiring pads for electrically connecting one cable wiring part 60 to the plurality of wiring pads 56a of the FPC 56, respectively, and the plurality of wiring pads may be wiring-connected to the plurality of cables 58 of, respectively, in advance.

In this case, first, the plurality of wiring pads 56a, and the plurality of wiring pads of the cable wiring part 60, are electrically connected to each other by pasting the FPC 56 and the wiring board provided with the cable wiring part 60 to each other such that the plurality of wiring pads 56a of the FPC 56 and the plurality of wiring pads of the cable wiring part 60 come into contact with each other.

Next, the pasting of the FPC 56 integrated with the cable wiring part 60 to the ultrasonic oscillator array 50 may be performed similarly to the above-described example.

In this way, by performing wiring on a small-sized board including the flexible board, such as the FPC 56 in which the cables 58 are wired in advance and by pasting the small-sized board (the wiring pads 56a of the FPC 56) and the ultrasonic oscillator array 50 (the electrodes 52a of the electrode part 52) to each other, the wiring step of the ultrasonic oscillator can be simplified.

Alternatively, first, the pasting of the FPC 56 to the ultrasonic oscillator array 50 may be performed similarly to the above-described example, and next, the FPC 56 pasted on the ultrasonic oscillator array 50 and the wiring board provided with the cable wiring part 60 may be pasted to each other, similarly to the above-described example.

The pasting (that is, electrical connection) is also preferably performed using an anisotropic conductive sheet or an anisotropic conductive paste and is preferably performed by heat fusion, similarly to the electrical connection between the wiring pads 56a and the electrode 52a. In addition, this electrical connection is also not necessarily limited to the methods, and any kind of method may be performed using as long as the workability of wiring is not hindered and the difficulty of the operation step does not become high, and well-known methods, such as wire bonding and soldering, may be used.

Even in this case, the wiring step of the ultrasonic oscillator can be simplified similarly.

Here, in the invention, size reduction of the ultrasonic oscillator unit 46 is required. Therefore, it is preferable to use the flexible wiring board, such as the FPC 56, as the wiring board of the invention to be electrically connected to the electrode part 52 as in the illustrated example. However, the invention is not limited to this, and the rigid wiring board, such as the PCB or the PWB, may be used or the flexible wiring board and the rigid wiring board may be used in combination.

Additionally, in the cable wiring part 60, the plurality of cables 58 are ultrafine. Therefore, in order to stably dispose the cable wiring part 60 within the sheathing member 41 of the distal end part 40, it is preferable that the cable wiring part 60 is configured using the rigid wiring board, such as the PCB or the PWB. However, the invention is not limited to this, and the cable wiring part 60 may be configured using the flexible board, such as the FPC or the flexible board and the rigid wiring board may be used in combining. That is, the cable wiring part 60 may be configured using the wiring boards used for the invention as described above.

Additionally, the cable unit 62 includes the wiring board, such as the FPC 56, and the cable wiring part 60 as described above, and is a cable unit in which the plurality of wiring pads 56a of the FPC 56, and the plurality of cables 58 wiring-connected to the cable wiring part 60, are connected to each other, respectively. Here, since the wiring board electrically connected to the electrode part 52 and the wiring board constituting the cable wiring part 60 are not particularly limited, the cable unit 62 can be configured using various wiring boards. However, it is preferable to configure the cable unit 62, using the multilayer interconnection board in which the flexible wiring board, such as the FPC 56, and the rigid wiring boards, such as the PCB or PWB having the cable wiring part 60, among the various wiring boards, are provided, that is, are integrated with each other.

In the invention, at least a portion of the cable wiring part 60 needs to be included in the recess 54a of the backing material layer 54. That is, the recess 54a needs to be a space that can house at least a portion of the cable wiring part 60. In addition, in the ultrasonic oscillator unit 46 of the invention, as illustrated in FIGS. 3 and 4, two wiring pads 57 and therefore, two cable wiring parts 60 are housed in the semicircular columnar recess 54a, and as illustrated in FIG. 5, the cable wiring parts 60, wiring portions of the numerous cables 58, and portions of extending portions in which the numerous cables 58 extend are housed in the recess 54a so as to be directed to the center side of the backing material layer 54 from both the outer side surfaces of the backing material layer 54. In this way, by housing the cable wiring part 60, to which the numerous cables 58 are wiring-connected, in the recess 54a of the backing material layer 54, the space within the ultrasonic observation part 36 of the distal end part 40 of the ultrasonic endoscope 12 can be effectively used in the invention. As a result, size reduction of an ultrasonic oscillator unit and eventually size reduction of the ultrasonic endoscope 12 can be achieved.

Here, in the ultrasonic oscillator unit 46 of the invention, as illustrated in FIG. 5, it is preferable that a gap of the recess 54a between the cable wiring parts 60 and the numerous cables 58 housed within the semicircular columnar recess 54a surrounded by the cable units 62 on both the outer side surfaces of the backing material layer 54 and the backing material layer 54, and the backing material layer 54, that is, a space, which is not occupied by the cable wiring parts 60 within the recess 54a of the backing material layer 54, the wiring portions of the numerous cables 58, and the extending portions of the wiring portions, is filled with a filler and is used as a filler layer 74.

In addition, in a case where the ultrasonic oscillator unit 46 of the invention is attached to the sheathing member 41 of the distal end part 40 of the ultrasonic endoscope 12, it is preferable that a gap (space) between the ultrasonic oscillator unit 46, that is, the acoustic lens 66, the cable units 62, the filler layer 74, and the numerous cables 58, and the sheathing members 41, is filled with a filler having excellent heat dissipation and is used as a filler layer 76.

Such filler layers 74 and 76 are provided in order to fill the gap within the recess 54a of the backing material layer 54, and the gap between the ultrasonic oscillator unit 46 and the sheathing member 41, and can fix the cable wiring parts 60, and the wiring portions of the numerous cables 58 and portions of the extending portions thereof, to prevent disconnection of the cables 58 and the like. In this way, by covering the cable wiring parts 60 and at least portions of the numerous cables 58 with the filler and forming the filler layers 74 and/or 76, and the portions of the cables 58 during an handling of an assembly of the ultrasonic oscillator unit 46 of the invention and the ultrasonic observation part 36 can be protected.

Moreover, it is preferable that the acoustic impedances of the filler layer 74 and the backing material layer 54 are matched with each other such that the ultrasonic waves, which are oscillated from the ultrasonic oscillator array 50 and propagated to a lower side thereof, are not reflected at a boundary between the filler layer 74 and the backing material layer 54 and such that the ultrasonic waves oscillated from the ultrasonic oscillator array 50 can be reflected in an observation target or its peripheral part and can sufficiently dampen the ultrasonic waves propagated to the lower side of the ultrasonic oscillator array 50. For that reason, in a case where the acoustic impedance of the filler layer 74 is defined as Zp (kg/m² s) and the acoustic impedance of the backing material layer 54 is defined as Zb (kg/m² s), it is preferable that an acoustic impedance reflectivity Q of the filler layer 74 and the backing material layer 54 expressed by the following Equation (1) is 50% or less.

$$Q = 100 \times |Zp - Zb|/(Zp + Zb) \qquad (1)$$

The acoustic impedance reflectivity Q is an index showing the easiness of reflection of the ultrasonic waves (sound beams) on a boundary surface between the filler layer 74 and the backing material layer 54, that is, shows that the acoustic impedance of the filler layer 74 and the acoustic impedance of the backing material layer 54 are matched with each other as the value thereof is closer to 0%. In a case where the above acoustic impedance reflectivity is about 50% or less, the noise caused by the ultrasonic waves propagated to the lower side of the ultrasonic oscillator array 50 can be processed so as not to become a problem in creating the ultrasound image in the ultrasonic wave processor device 14 using the ultrasonic signals received in the ultrasonic oscillator array 50.

In addition, also in the filler layer 76, it is more preferable to take the matching of the acoustic impedance with the backing material layer 54, similarly to the filler layer 74.

Additionally, in a case where the ultrasonic waves are oscillated from the ultrasonic oscillator array 50 of the ultrasonic oscillator unit 46, the driving signals transmitted from the ultrasonic wave processor device 14 to the ultrasonic oscillator array 50 become thermal energy and the ultrasonic oscillator array 50 generates heat. Therefore, it is preferable that the filler layer 76 has heat dissipation. For that reason, it is preferable that the thermal conductivity of the filler layer 76 is 1.0 W/mK or more.

In addition, also in the filler layer 74, it is more preferable to use the filler having excellent heat dissipation similarly to the filler layer 76.

Here, in the ultrasonic oscillator unit 46 illustrated in FIG. 5, it is preferable that the electrical connection between the electrodes 52a (wiring pads 56a) of the FPC 56 of the cable unit 62 and the electrode part 52 of the ultrasonic oscillator array 50 is performing by joining the wiring pads 56a on the side surfaces of the distal end portion of the FPC 56 and the electrodes 52a of the electrode part 52 on each outer side surface (the end surfaces of the ultrasonic oscillators 48) of the ultrasonic oscillator array 50 to each other, using an anisotropic conductive sheet or anisotropic conductive paste or by heat fusion. However, it is needless to say that the invention is not limited to this.

Figure 10:
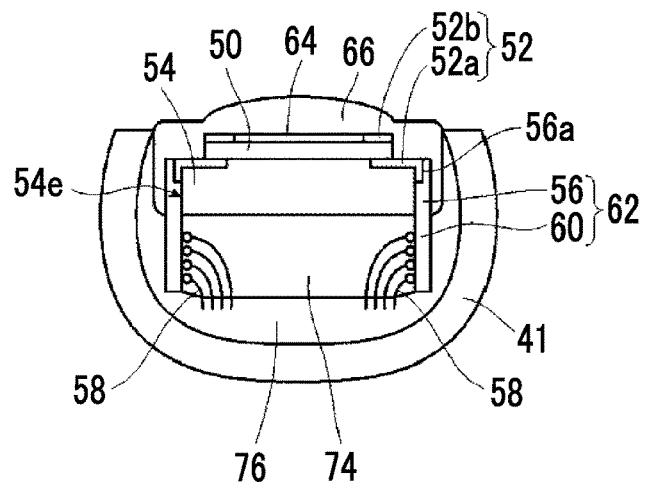
FIG. 10 is a cross-sectional view of another example of the ultrasonic observation part of the distal end part of the ultrasonic endoscope of the invention.

For example, as illustrated in FIG. 10, the electrodes 52a of the electrode part 52 of the ultrasonic oscillator array 50 may be made to extend from the top surface 54b (the arrangement surface of the ultrasonic oscillators 48) of the backing material layer 54 to an outer side surface 54e, the thickness of portions of at least the wiring pads 56a of the FPC 56 of the cable unit 62 may be made smaller by that amount, and the extending portions of the electrodes 52a extending to the outer side surface 54e of the backing material layer 54 and the portions of the wiring pads 56a of the FPC 56 of which the thickness is made smaller are pasted and joined to each other and both may be electrically connected to each other solder or the like.

Figure 11:
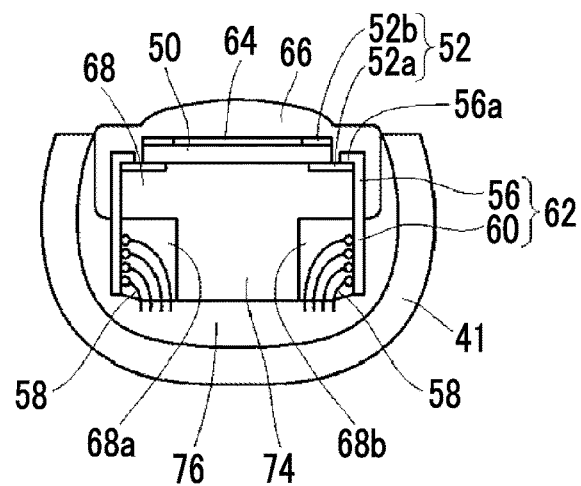
FIG. 11 is a cross-sectional view of still another example of the ultrasonic observation part of the distal end part of the ultrasonic endoscope of the invention.

Additionally, in the example illustrated in FIG. 11, the portions of at least the wiring pads 56a of the FPC 56 of the cable unit 62 may be pasted and joined to the electrodes 52a of the electrode part 52 of the ultrasonic oscillator array 50 disposed on a top surface of a backing material layer 68 illustrated in FIG. 7 that is the arrangement surface of the ultrasonic oscillators 48, and both may be electrically connected to each other.

In addition, although the backing material layer 68 having the counterbore (recess) 68a that does not penetrate is used in the example illustrated in FIG. 11, the invention is not limited to this. The semicylindrical backing material layer 54 having the penetrating semicircular columnar recess 54a illustrated in FIGS. 5, 6, and 10 may be used, the backing material layers 69 and 70 that respectively have the recesses 69a and 70a that do not penetrate as illustrated in FIGS. 8 and 9 may be used, or backing material layers having other shapes and structures may be used.

In addition, in the examples illustrated in FIGS. 5, 10, and 11, the recesses are provided from the outer side surfaces of the backing material layer 54 or 68 toward the center side thereof. However, the invention is not limited to this.

Figure 11A:
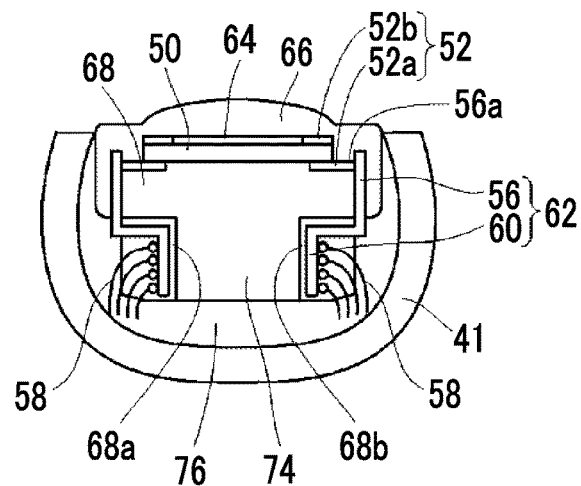
FIG. 11A is a cross-sectional view of a still further example of the ultrasonic observation part of the distal end part of the ultrasonic endoscope of the invention.

As illustrated in FIG. 11A, it is also possible to provide the cable wiring part 60 on each outer side surfaces of the backing material layer 68. However, as illustrated in FIG. 11A, since it is necessary to bend the wiring board constituting the cable unit 62 toward the center side along an inner wall surface of the recess 68a of the backing material layer 68 to provide the cable wiring parts 60 on the outsides thereof, there is a concern that the structure of the wiring board, such as the FPC, becomes complicated. That is, in the example illustrated in FIG. 11A, the portion of the FPC 56 is pasted to the electrode part 52 on each outer side surface of the ultrasonic oscillator array 50, similarly to the examples illustrated in FIGS. 5, 10, and 11, a wiring board portion following the FPC 56 is bent toward the center side along the inner wall surface of the recess 68a and subsequently bent downward in the drawing, and the cable wiring part 60 is provided on each outer side surface of the wiring portion that is bent downward.

In addition, also in the example illustrated in FIG. 11A, similarly to the example illustrated in FIG. 11, the backing material layer 54 illustrated in FIGS. 5, 6, and 10 may be used, the backing material layers 69 and 70 illustrated in FIGS. 8 and 9 may be used, and backing material layers having other shapes and structures may be used.

The endoscope observation part 38 is constituted of an observation window 78, an objective lens 80, a solid-state imaging element 82, an illumination window 84, a washing nozzle 86, a wiring cable 88, and the like.

The distal end part 40 is detached obliquely upward of the observation window 78. The reflected light of the region to be observed, which has been incident from the observation window 78, is focused on an imaging surface of the solid-state imaging element 82 by the objective lens 80. The solid-state imaging element 82 photoelectrically converts of the reflected light of the region to be observed transmitted through the observation window 78 and the objective lens 80 and focused on the imaging surface, and outputs imaging signals. As the solid-state imaging element 82, a charge-coupled device (CCD), a complementary metal oxide semi-conductor (CMOS), or the like can be used. The captured image signals output by the solid-state imaging element 82 are transmitted to the endoscope processor device 16 by the universal cord 26 via the wiring cable 88 extending from the insertion part 22 to the operating part 24. The endoscope processor device 16 performs various kinds of signal processing and image processing with respect to the transmitted imaging signals, and displays the processed signals as the endoscopic optical image on the monitor 20.

Illumination windows 84 are provided on both sides with the observation window 78 interposed therebetween. An exit end of the light guide (not illustrated) is connected to the illumination windows 84. The light guide is provided to extend from the insertion part 22 to the operating part 24 and has an incident end connected to the light source device 18 connected via the universal cord 26. The illumination light emitted by the light source device 18 is transmitted to the light guide and is radiated from the illumination windows 84 to a region to be observed.

Additionally, the washing nozzle 86 jets air or washing water toward the observation window 78 and the illumination windows 84 through the air/water supply pipe line within the ultrasonic endoscope 12 from the water supply tank 21a in order to clean the surfaces of the observation window 78 and the illumination windows 84.

Additionally, the distal end part 40 is provided with the treatment tool delivery port 44. The treatment tool delivery port 44 is connected to a treatment tool channel 45 to be inserted through the inside of the insertion part 22, and a treatment tool inserted into a treatment tool insertion port 30 is introduced into the body cavity via the treatment tool channel 45 from the treatment tool delivery port 44. In addition, although the treatment tool delivery port 44 is located between the ultrasonic observation part 36 and the endoscope observation part 38, it is preferable to dispose the treatment tool delivery port 44 close to the ultrasonic observation part 36 in a case where the movement of the treatment tool introduced into the body cavity from the treatment tool delivery port 44 is confirmed with the ultrasound image.

Although not illustrated, a rising stand that changes a delivery direction of the treatment tool introduced into the body cavity from the treatment tool delivery port 44 may be provided inside the treatment tool delivery port 44. A wire (not illustrated) is attached to the rising stand, the standing angle of the rising stand is changed by a push/pull operation resulting from the operation of a standing lever (not illustrated) of the operating part 24, and thereby the treatment tool is delivered in a desired direction.

In a case where the inside of the body cavity is observed by the ultrasonic endoscope 12, first, the insertion part 22 is inserted into the body cavity and searches for the region to be observed while the endoscopic optical image acquired in the endoscope observation part 38 is observed by the monitor 20.

Next, in a case where the distal end part 40 reaches the region to be observed and an instruction for acquiring the ultrasonic tomographic image is made, a driving control signal is input from the ultrasonic wave processor device 14 via the cables 58 within the ultrasonic endoscope 12, the cable unit 62, and the electrode part 52 to the ultrasonic oscillators 48. In a case where the driving control signal is input, a regular voltage is applied to both the electrodes of each ultrasonic oscillator 48. Then, the piezoelectric bodies of the ultrasonic oscillators 48 are excited, and the ultrasonic waves are emitted to the region to be observed via the acoustic lens 66.

The echo signals from the region to be observed are received by the ultrasonic oscillators 48 after the radiation of the ultrasonic waves. The radiation of the ultrasonic waves and the reception of the echo signals are repeatedly performed while the ultrasonic oscillators 48 to be driven are shifted by the electronic switch, such as the multiplexer. Accordingly, the region to be observed is scanned with the ultrasonic waves. In the ultrasonic wave processor device 14, the ultrasonic tomographic image is created on the basis of the detection signals output from the ultrasonic oscillators 48 upon receiving the echo signals. The created ultrasonic tomographic image is displayed on the monitor 20.

The ultrasonic oscillator unit 46 of the invention can be manufactured as follows.

The method of manufacturing the ultrasonic oscillator unit 46 is characterized by simplifying the wiring step of the ultrasonic oscillator array 50 to the numerous ultrasonic oscillators 48. Although the wiring step will be described in detail, it is assumed that manufacture of the individual constituent elements and the individual members of the ultrasonic oscillator unit 46 is made.

Additionally, although the method of manufacturing the ultrasonic oscillator unit 46 of the invention will be described with reference to FIGS. 12 to 17, FIGS. 12 to 17 are not views illustrating actual constituent elements and members and are views for the description that only portions required for description are illustrated and portions that are not used for description are omitted.

Figure 12:
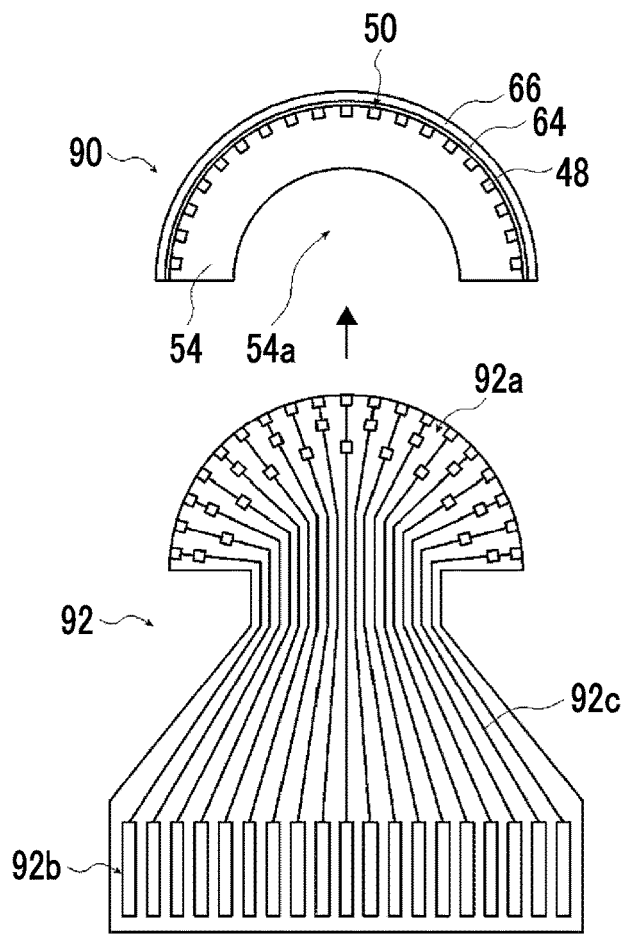
FIG. 12 is an illustrative view illustrating one step of a method of manufacturing the ultrasonic oscillator unit of the invention.

First, as illustrated in FIG. 12, an ultrasonic oscillator assembly 90, which is a laminated body of the backing material layer 54, the ultrasonic oscillator array 50 including the plurality of ultrasonic oscillators 48, the acoustic matching layer 64, and the acoustic lens 66, is prepared.

Additionally, as illustrated in FIG. 12, an inspection flexible board 92 having a plurality of connecting electrodes 92a that can be electrically connected to the plurality of electrodes 52a (refer to FIGS. 4 and 5) of the electrode part 52 of the ultrasonic oscillator array 50 due to pasting, a plurality of inspecting electrodes 92b having a larger inter-electrode pitch than the plurality of connecting electrodes 92a, and wiring lines 92c for electrically connecting the connecting electrodes and the inspecting electrodes to each other, respectively, is prepared on an outer side surface of the ultrasonic oscillator array 50.

Figure 13:
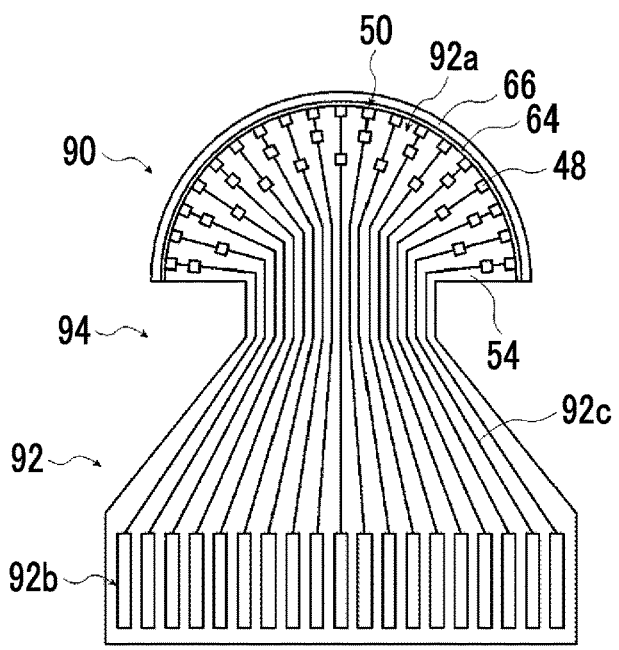
FIG. 13 is a plan view illustrating an intermediate product manufactured in the manufacturing method of the invention illustrated in FIG. 12.

Next, as illustrated in FIG. 13, the inspection flexible board 92 is pasted to the electrode part 52 of the ultrasonic oscillator array 50 and the plurality of connecting electrodes 92a and the plurality of electrodes 52a are electrically connected to each other such that the plurality of connecting electrodes 92a of the inspection flexible board 92 and the plurality of electrodes 52a of the electrode part 52 of the ultrasonic oscillator array 50 of the ultrasonic oscillator assembly 90 are joined to each other.

In this way, as illustrated in FIG. 13, an ultrasonic oscillator inspection assembly 94 in which the inspection flexible board 92 is pasted to the ultrasonic oscillator assembly 90 is manufactured.

The plurality of ultrasonic oscillators 48 of the ultrasonic oscillator array 50 are inspected using the plurality of inspecting electrodes 92b of the ultrasonic oscillator inspection assembly 94. Since the plurality of inspecting electrodes 92b has an inter-electrode pitch larger than the plurality of electrodes 52a of the electrode part 52 of the ultrasonic oscillator array 50, for example, a cable end part is a clip-like connector. Thus, since it is possible to use a holding device for establishing an electrical connection by sandwiching the inspecting electrodes 92b with the clip-like connector, the inspection can be easily performed.

In the related art, the plurality of ultrasonic oscillators 48 of the ultrasonic oscillator array 50 can be inspected only after the plurality of cables 58 are connected to the plurality of electrodes 52a of the electrode part 52 of the ultrasonic oscillator array 50 of the ultrasonic oscillator assembly 90. Thus, since the plurality of cables 58 that are ultrafine and expensive cannot be used in a case where the ultrasonic oscillators 48 do not pass inspection, the costs are increased. However, cost reduction can be achieved by adopting the structure of the ultrasonic oscillator unit 46 of the invention.

Figure 14:
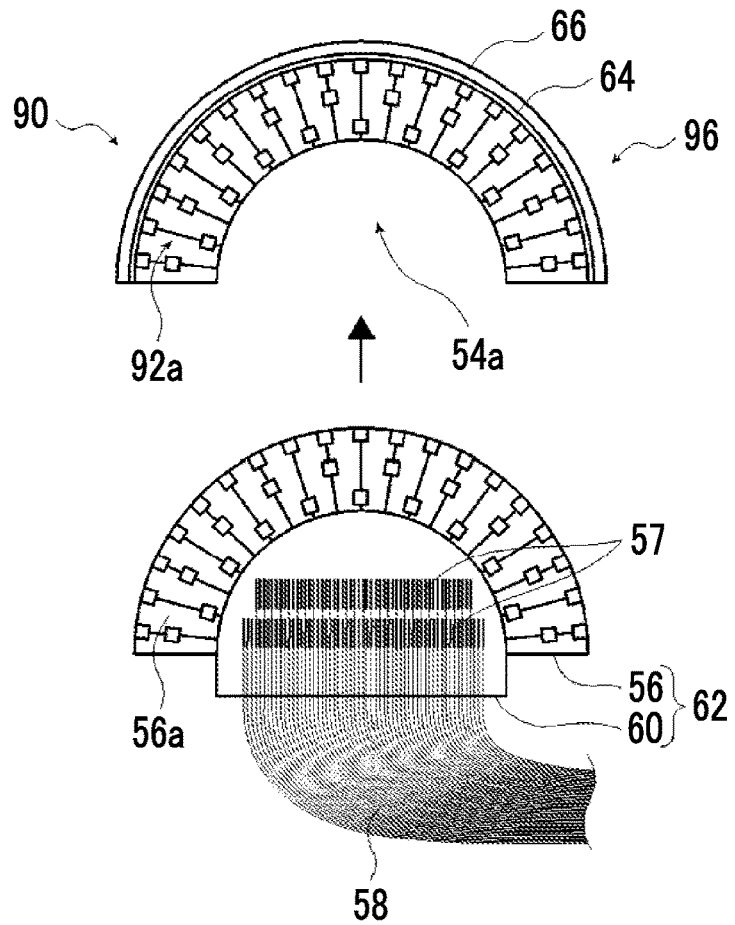
FIG. 14 is an illustrative view illustrating another step of the method of manufacturing the ultrasonic oscillator unit of the invention.

Next, as illustrated in FIG. 14, the ultrasonic oscillator assembly 96 to which the plurality of connecting electrodes 92a are pasted by cutting the inspection flexible board 92 along the semicircular shape of the recess 54a of the backing material layer 54 of the ultrasonic oscillator assembly 90 from the ultrasonic oscillator inspection assembly 94 in which the respective ultrasonic oscillators 48 of the ultrasonic oscillator array 50 have passed inspection is manufactured.

In addition, in this case, the pasted inspection flexible board 92 may be peeled and removed from the ultrasonic oscillator inspection assembly 94.

Meanwhile, as illustrated in FIG. 14, prepared is the cable unit 62, including the multilayer interconnection board, such as a multilayer FPC, which has the FPC 56 having the wiring pads 56a capable of being joined to the plurality of connecting electrodes 92a or the plurality of electrodes 52a of the electrode part 52 of the ultrasonic oscillator array 50 by pasting, and the wiring board in which the cable wiring part 60 having the wiring pads 57 to which the plurality of cables 58 are wiring-connected in advance is formed.

In addition, the cable wiring part 60 of the cable unit 62 is formed such that at least some thereof, in the illustrated example, two wiring pads 57 are housed in the semicircular recess 54a of the backing material layer 54. In the illustrated example, the wiring board in which the cable wiring part 60 is formed has the same semicircular shape as the semicircular recess 54a of the backing material layer 54.

The plurality of connecting electrodes 92a or the plurality of electrodes 52a, and the wiring pads 56a are electrically connected to each other by pasting the ultrasonic oscillator assembly 96 or 90 and the cable unit 62 illustrated in FIG. 14 to each other such that the plurality of connecting electrodes 92a or the plurality of electrodes 52a, and the wiring pads 56a of the FPC 56 are joined to each other. In this case, the cable unit 62 pastes the cable wiring part 60 to the ultrasonic oscillator assembly 96 or 90 toward the inside such that the cable wiring part 60 is housed in the recess 54a of the backing material layer 54.

Figure 15:
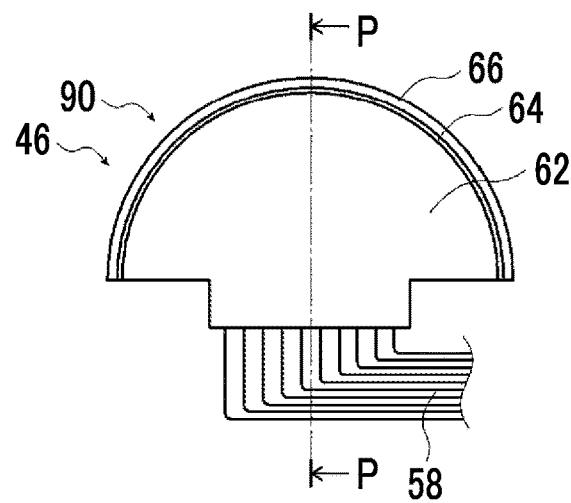
FIG. 15 is a plan view illustrating the ultrasonic oscillator unit manufactured in the manufacturing method of the invention.
Figure 16:
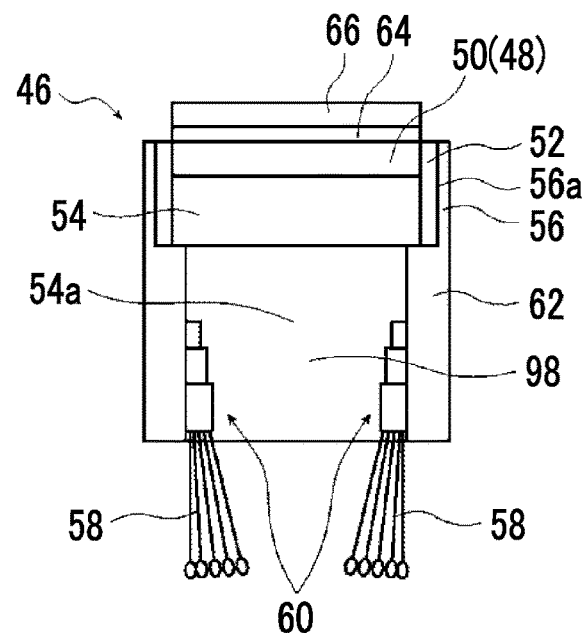
FIG. 16 is a cross-sectional view cut along line P-P illustrated in FIG. 15.
Figure 17:
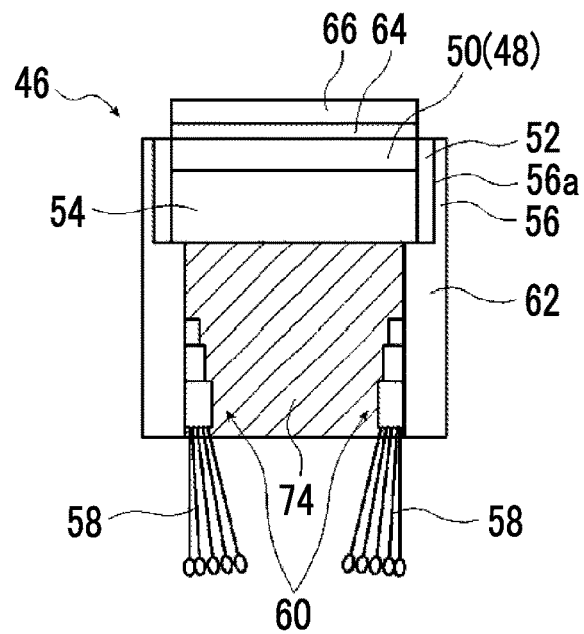
FIG. 17 is a cross-sectional view of the ultrasonic oscillator unit manufactured in the manufacturing method of the invention.

In this way, the ultrasonic oscillator unit 46 of the invention illustrated in FIGS. 15 and 16 can be manufactured. FIG. 15 is a side view of the ultrasonic oscillator unit 46. As illustrated in FIG. 15, only an outer side surface of the cable unit 62 is visible from the outside, and the cable wiring part 60 is not visible from the outside.

Meanwhile, FIG. 16 is a sectional view cut along line P-P of FIG. 5 and is a cross-sectional view of the ultrasonic oscillator unit 46. As illustrated in FIG. 16, the cable wiring part 60 of each cable unit 62 is housed within the recess 54a of the backing material layer 54.

Additionally, although the recess 54a of the backing material layer 54 is filled with the cable wiring part 60 and the plurality of cables 58 of the cable unit 62, the entire recess is not filled and a gap 98 is present.

Subsequently, the filler is injected into the gap 98 in consideration of backing performance, sound compatibility, heat dissipation, and the like to make the filler layer 74. In this way, the final ultrasonic oscillator unit 46 of the invention can be manufactured.

Basically, the ultrasonic oscillator unit of the invention is configured as described above and is manufactured as described above.

Meanwhile, in the invention, the backing material layer 54 of the illustrated example has the semicylindrical shape (doughnut shape), and may be arranged such that at least a portion of the cable wiring part is included in a circular-arc upper half in a case where the same circular arc is drawn.

Additionally, although the counterbore is provided in the backing material layer of an overlap part between the above circular arc and the cable wiring part 60 such that the cable wiring part 60 does not interfere with the backing material layer 54, just a space may be formed.

In this way, in the ultrasonic oscillator unit of the invention, the space within the ultrasonic endoscope 12 can be effectively used by providing the recess 54a of the backing material layer 54 from the outer side surfaces of the backing material layer 54 toward the center side thereof and by performing the protection of the portions of the cables on a central part side of the ultrasonic observation part 36 of the distal end part 40 of the ultrasonic endoscope 12.

Additionally, the electrode wiring and the pasting between the cable unit 62 including the small-sized board (wiring pads 56a of the FPC 56) including the flexible board, such as the FPC 56 and the ultrasonic oscillator array 50 (the electrodes 52a of the electrode part 52) may be performed on the outer side surfaces (the end surfaces of the ultrasonic oscillators 48) of the ultrasonic oscillator array 50.

Although the ultrasonic oscillator unit related to the invention and the ultrasonic endoscope using the same have been described above in detail, it is natural that the invention is not limited to the above examples, and various improvements and modifications may be made without departing from the scope of the invention.

EXPLANATION OF REFERENCES

10: ultrasonic inspection system
12: ultrasonic endoscope
14: ultrasonic wave processor device
16: endoscope processor device
18: light source device
20: monitor
21a: water supply tank
21b: suction pump
22: insertion part
24: operating part
24: universal cord
28a: air/water supply button
28b: suction button
29: angle knob
29, 30: treatment tool insertion port (forceps port)
32a: ultrasonic wave connector
32b: endoscope connector
32c: light source connector
34a: air/water supply tube
34b: suction tube
36: ultrasonic observation part
38: endoscope observation part
40: distal end part
41: sheathing member
42: bending part
43: flexible part
44: treatment tool insertion port
46: ultrasonic oscillator unit
48: ultrasonic oscillator
50: ultrasonic oscillator array 52: electrode part
52a: individual electrode
52b: common electrode
54, 68, 69, 70: backing material layer
54a, 68a, 69a, 70a: recess
54b: outer surface (top surface)
54c: lower surface
54d, 68c, 69c, 70c: bottom surface (inner surface)
54e, 68b, 69b, 70b: outer side surface
56: flexible printed wiring board (FPC)
56a, 56b, 57: wiring pad
58: cable
60: cable wiring part
62: cable unit
64: acoustic matching layer
66: acoustic lens
74, 76: filler material layer
78: observation part
80: objective lens
82: solid-state imaging element
84: illumination window
86: washing nozzle
88: wiring cable
90, 96: ultrasonic oscillator assembly
92: flexible board for inspection
92a: connecting electrode
92b: Inspecting electrode
92c: wiring line
94: ultrasonic oscillator inspection assembly
98: gap
EL: longitudinal direction (elevation direction)
AZ: parallel direction (azimuth direction)

What is claimed is:

1. An ultrasonic oscillator unit comprising:
an ultrasonic oscillator array in which a plurality of ultrasonic oscillators are arranged outward in a circular-arc shape so as to have a circular-arc surface resulting from the arrangement of the plurality of ultrasonic oscillators and end surfaces perpendicular to the circular-arc surface;
an electrode part having a plurality of electrodes provided on a side of one of the end surfaces of the ultrasonic oscillator array and electrically connected to the plurality of ultrasonic oscillators, respectively;
a backing material layer that is disposed on a back surface of the ultrasonic oscillator array, which is an inward surface of the ultrasonic oscillator array, the backing material layer having an outer surface having a circular-arc shape section, and the backing material layer being provided with recesses under the circular-arc shape section of the backing material and opposite to the outer surface of the backing material layer;
a wiring board having a plurality of wiring lines electrically connected to the plurality of electrodes of the electrode part; and
cable wiring parts which are respectively disposed on both of outer side surfaces of the backing material layer, in which a plurality of cables connected to the plurality of wiring lines, respectively, are wiring-connected,
wherein the recesses of the backing material layer are on a surface of the outer side surfaces of the backing material layer which is a surface having circular-arc cross-section perpendicular to an elevation direction which is a longitudinal direction of the ultrasonic oscillator array, and the recesses of the backing material layer are recessed in the elevation direction on a back side of a rear surface of the ultrasonic oscillator array, and are provided on both of the outer side surfaces of the backing material layer in order to dispose the respective cable wiring parts, and
at least a portion of the cable wiring parts is included in the recesses of the backing material layer.

2. The ultrasonic oscillator unit according to claim 1,
wherein the backing material layer has a bow shape, a semicylindrical shape, a shape obtained by cutting a column with a plane parallel to a centerline, or a semicircular columnar shape, and
bottom surfaces of the backing material layer, the bottom surfaces being surfaces opposite from the back surface of the ultrasound oscillator array and perpendicular to the outer side surface of the backing material layer, are on a same plane.

3. The ultrasonic oscillator unit according to claim 2,
wherein the recesses of the backing material layer are provided from the outer side surface of the backing material layer toward the center side thereof.

4. The ultrasonic oscillator unit according to claim 3,
wherein the recesses are formed by performing counter-boring from the outer side surface of the backing material layer toward the center side thereof, and
wherein the recesses include a bow-shaped recess, a semicircular recess, a polygonal recess, a pyramidal recess, or a conical recess, viewing from a direction perpendicular to the outer side surface of the backing material layer.

5. The ultrasonic oscillator unit according to claim 2,
wherein the recesses are formed by performing counter-boring from the outer side surface of the backing material layer toward the center side thereof, and
wherein the recesses include a bow-shaped recess, a semicircular recess, a polygonal recess, a pyramidal recess, or a conical recess, viewing from a direction perpendicular to the outer side surface of the backing material layer.

6. The ultrasonic oscillator unit according to claim 1,
wherein the recesses of the backing material layer are provided from the outer side surface of the backing material layer toward the center side thereof.

7. The ultrasonic oscillator unit according to claim 6,
wherein the recesses are formed by performing counter-boring from the outer side surface of the backing material layer toward the center side thereof, and
wherein the recesses include a bow-shaped recess, a semicircular recess, a polygonal recess, a pyramidal recess, or a conical counterbore, viewing from a direction perpendicular to the outer side surface of the backing material layer.

8. The ultrasonic oscillator unit according to claim 1,
wherein the recesses are formed by performing counter-boring from the outer side surface of the backing material layer toward the center side thereof, and
wherein the recesses include a bow-shaped recess, a semicircular recess, a polygonal recess, a pyramidal recess, or a conical recess, viewing from a direction perpendicular to the outer side surface of the backing material layer.

9. The ultrasonic oscillator unit according to claim 1,
wherein the recesses of the backing material layer are formed so as to enlarge in a direction away from the ultrasonic oscillator array.

10. The ultrasonic oscillator unit according to claim 1, wherein the cable wiring parts are provided on a surface of the wiring board on the center side of the backing material layer.

11. The ultrasonic oscillator unit according to claim 1, wherein gaps of the recesses between the cable wiring parts housed in the recesses of the backing material layer and the backing material layer is filled with a filler.

12. The ultrasonic oscillator unit according to claim 11, wherein at least a portion of the cable wiring parts is covered with the filler.

13. The ultrasonic oscillator unit according to claim 1, further comprising:
   a cable unit that includes the wiring board and the cable wiring parts and is formed by connecting the plurality of wiring lines of the wiring board and the plurality of cables wiring-connected to the cable wiring parts, respectively, to each other.

14. The ultrasonic oscillator unit according to claim 13, wherein the cable unit is a multilayer interconnection board having a flexible printed wiring board that is the wiring board, and a rigid printed wiring circuit board having the cable wiring parts.

15. The ultrasonic oscillator unit according to claim 14, wherein the flexible printed wiring board is electrically connected to the electrode part by heat fusion and is disposed on one of the end surfaces of the ultrasonic oscillator array.

16. The ultrasonic oscillator unit according to claim 14, wherein the flexible printed wiring board is electrically connected to the electrode part using an anisotropic conductive sheet or anisotropic conductive paste and is disposed on one of the end surfaces of the ultrasonic oscillator array.

17. The ultrasonic oscillator unit according to claim 14, wherein the flexible printed wiring board is disposed on one of the end surfaces of the ultrasonic oscillator array, and a filler is injected into a gap of the recesses of the backing material layer, in which the cable wiring parts are housed, to fill the gap.

18. The ultrasonic oscillator unit according to claim 1, wherein the wiring board has a flexible printed wiring board, a printed wiring circuit board, or both the boards.

19. An ultrasonic endoscope for imaging an inside of a body cavity of a subject to acquire an ultrasound image and an endoscopic image, respectively, the ultrasonic endoscope comprising:
   an insertion part to be inserted into the body cavity;
   an ultrasonic observation part that is provided at a distal end of the insertion part, includes the ultrasonic oscillator unit according to claim 1, and acquires the ultrasound image;
   an endoscope observation part that is provided closer to a proximal end side than the ultrasonic observation part in the insertion part and includes an illumination window that emits illumination light that illuminates a region to be imaged within the body cavity, and an imaging element that images the region to be imaged that is illuminated with the illumination light from the illumination window; and
   a treatment tool channel that is provided closer to a proximal end side than the ultrasonic observation part in the insertion part and includes a treatment tool delivery port for inserting a treatment tool into the body cavity.

* * * * *